(12) United States Patent
Iwamoto et al.

(10) Patent No.: US 9,314,439 B2
(45) Date of Patent: Apr. 19, 2016

(54) COMPOSITION AND METHOD FOR MUSCLE REPAIR AND REGENERATION

(71) Applicant: Thomas Jefferson University, Philadelphia, PA (US)

(72) Inventors: Masahiro Iwamoto, Villanova, PA (US); Maurizio Pacifici, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 14/308,570

(22) Filed: Jun. 18, 2014

(65) Prior Publication Data

US 2014/0303223 A1 Oct. 9, 2014

Related U.S. Application Data

(63) Continuation of application No. 13/819,914, filed as application No. PCT/US2011/049905 on Aug. 31, 2011.

(60) Provisional application No. 61/378,996, filed on Sep. 1, 2010.

(51) Int. Cl.
*A61K 31/415* (2006.01)
*A61K 31/192* (2006.01)
(Continued)

(52) U.S. Cl.
CPC .............. *A61K 31/192* (2013.01); *A61K 31/185* (2013.01); *A61K 31/19* (2013.01); *A61K 31/415* (2013.01); *A61K 35/12* (2013.01); *A61K 45/06* (2013.01)

(58) Field of Classification Search
CPC combination set(s) only.
See application file for complete search history.

(56) References Cited

U.S. PATENT DOCUMENTS 5,624,957 A 4/1997 Swann et al.
5,760,084 A 6/1998 Swann et al.
(Continued)

FOREIGN PATENT DOCUMENTS

JP 2005-206544 A 8/2005
WO WO-01/80894 A2 11/2001
(Continued)

OTHER PUBLICATIONS

Einhorn, Bone Regeneration: New Findings and Potential Clinical Applications, Journal of the American Academy of Orthopaedic Surgeons, 2001, vol. 9 (3), pp. 157-165.*

(Continued)

*Primary Examiner* — San-Ming Hui
*Assistant Examiner* — Andrew Lee
(74) *Attorney, Agent, or Firm* — Clark & Elbing LLP; Kristina Bieker-Brady

(57) ABSTRACT

The invention provides methods for muscle repair or regeneration comprising administering therapeutically effective amounts of RAR agonists or stem cells that are pretreated with contact with a RAR agonist to a subject at a site of muscle damage. Additionally, the invention provides compositions comprising RAR agonist treated stem cells and methods of use of said cells for muscle repair or regeneration. In one embodiment, the stem cells are mesenchymal stem cells. In one embodiment, the RAR agonist is an RARγ agonist. In one embodiment, administration of the RAR agonist is begun during a period of increased endogenous retinoid signaling in the subject resulting from incurrence of the damaged muscle tissue.

23 Claims, 5 Drawing Sheets

(51) Int. Cl.
- A61K 31/185 (2006.01)
- A61K 31/19 (2006.01)
- A61K 35/12 (2015.01)
- A61K 45/06 (2006.01)

(56) References Cited

U.S. PATENT DOCUMENTS

| | | |
|---|---|---|
| 6,187,950 B1 | 2/2001 | Song et al. |
| 6,313,168 B1 | 11/2001 | Pacifici et al. |
| 6,838,472 B2 | 1/2005 | Klaus et al. |
| 6,844,466 B2 | 1/2005 | Belloni et al. |
| 7,345,931 B2 | 3/2008 | Partsch et al. |
| 7,547,687 B2 | 6/2009 | Reading et al. |
| 2003/0113913 A1* | 6/2003 | Purton et al. ............ 435/372 |
| 2003/0114482 A1 | 6/2003 | Pacifici et al. |
| 2003/0125252 A1 | 7/2003 | Underhill et al. |
| 2005/0271705 A1 | 12/2005 | Hughes et al. |
| 2009/0176862 A1 | 7/2009 | Chandraratna et al. |
| 2009/0214493 A1 | 8/2009 | Pittenger et al. |
| 2013/0189319 A1* | 7/2013 | Cook et al. ............ 424/400 |
| 2014/0303223 A1 | 10/2014 | Iwamoto et al. |

FOREIGN PATENT DOCUMENTS

| | | |
|---|---|---|
| WO | WO-2010/071583 A1 | 6/2010 |
| WO | WO-2010/088735 A1 | 8/2010 |
| WO | WO-2012/125724 A1 | 9/2012 |
| WO | WO-2012/129562 A2 | 9/2012 |
| WO | WO-2012129562 A2 | 9/2012 |

OTHER PUBLICATIONS

Halevy et al., "Retinoic acid induces adult muscle cell differentiation mediated by the retinoic acid receptor-α." J Cell Physiol. 154(3):566-72 (1993).
Kennedy et al., "Retinoic acid enhances skeletal muscle progenitor formation and bypasses inhibition by bone morphogenetic protein 4 but not dominant negative β-catenin." BMC Biol. 7(67):1-21 (2009).
Neuville et al., "Retinoic acid regulates arterial smooth muscle cell proliferation and phenotypic features in vivo and in vitro through an RARα-dependent signaling pathway." Arterioscler Thromb Vasc Biol. 19:1430-6 (1999).
Pakala et al., "RARγ agonists inhibit proliferation of vascular smooth muscle cells." J Cardiovasc Pharmacol. 35(2):302-8 (2000).
Shimono et al., "A retinoid composition for rapid muscle repair and regeneration." Poster presented at BioTech 2010 Conference (Oct. 27, 2010).
Soprano et al., "Role of retinoic acid in the differentiation of embryonal carcinoma and embryonic stem cells." Vitam horm. 75:69-95 (2007).
Extended European Search Report for European Application 11822537.4, dated Feb. 7, 2014 (10 pages).
Shimono et al., "Potent inhibition of heterotopic ossification by nuclear retinoic acid receptor-γ agonist," Nat. Med. 17(4):454-60 (2011).
Di Rocco et al., "Selective RARγ agonist blocks heterotopic ossification and promotes skeletal muscle repair," ASBMR Oct. 4, 2013, (Abstract only).
Patent Examination Report No. 1 in Australian Patent Application No. 2011296080, issued Jul. 4, 2014 (4 pages).
Office Action and its English translation for Chinese Patent Application No. 201180052926.X, dated May 8, 2014 (19 pages).
Extended European Search Report for European Patent Application No. 11822537.4, dated Feb. 7, 2014 (10 pages).
Patent Examination Report No. 1 for New Zealand Patent Application No. 607547, dated Oct. 21, 2013 (3 pages).
Iwamoto et al., "Retinoic acid induces rapid mineralization and expression of mineralization-related genes in chondrocytes," Experimental cell research 207(2): 413-420 (1993).
Kaplan et al., "Derailing heterotopic ossification and RARing to go," Nature Medicine. 17:420-421 (2011).
Koyama et al., "Retinoid signaling is required for chondrocyte maturation and endochondral bone formation during limb skeletogenesis," Dev Biol. 208(2):375-91 (1999).
Krueger C et al., "Identification of Retinoic Acid in a High Content Screen for Agents that Overcome the Anti-Myogenic Effect of TGF-Beta-1," PLoS One. 5(11): e15511 (2010).
Le May et al., Chapter 3: Retinoid X Receptor Signalling in the Specification of Skeletal Muscle Lineage. Skeletal Muscle—From Myogenesis to Clinical Relations. Edited by Juliana Cseri, pp. 49-72 (2012).
Pacifici et al., "Vitamin A inhibits chondrogenesis but not myogenesis," Exp Cell Res. 129(2):469-74 (1980). Abstract Only.
Pacifici et al., Annual Report for U.S. Army Medical Research and Material Command, Oct. 2014, "Preventative Therapeutics for Heterotopic Ossification," (13 pages).
Rochette-Egly et al., "Dynamic and combinatorial control of gene expression by nuclear retinoic acid receptors (RARs)," Nuc Rec Sig. 7:1-18 (2009).
Shimono et al., "Inhibition of ectopic bone formation by a selective retinoic acid receptor α-agonist: A new therapy for heterotopic ossification?," Journal of Orthopaedic Research 28(2): 271-277 (2010).
Thacher et al., "Therapeutic applications for ligands of retinoid receptors," Curr Pharm Des. 6(1):25-58 (2000).
Weston et al., "Requirement for RAR-mediated gene repression in skeletal progenitor differentiation," J Cell Biol. 158(1):39-51 (2002).
Weston et al., "Revisiting the role of retinoid signaling in skeletal development," Birth Defects Res C Embryo Today. 69(2):156-73 (2003).
Williams et al., "Retinoic acid receptors are required for skeletal growth, matrix homeostasis and growth plate function in postnatal mouse," 328(2):315-27 (2009).
Yasuhara et al. "Wnt/β-catenin and retinoic acid receptor signaling pathways interact to regulate chondrocyte function and matrix turnover," Journal of Biological Chemistry 285(1):317-327 (2010).
Zasloff et al., "Treatment of patients who have fibrodysplasia ossificans progressiva with isotretinoin," Clin Orthop Relat Res. 346:121-9 (1998).
Danziger et al., "Automated site-directed drug design: a general algorithm for knowledge acquisition about hydrogen-bonding regions at protein surfaces," Proc R Soc Lond B Biol Sci. 236(1283):101-13 (1989).
English Translation of Office Action for Eurasian Patent Applicaiton No. 201370051, mailed Jun. 1, 2015 (4 pages).
International Search Report for International Application No. PCT/US2011/049905, dated May 3, 2012 (4 pages).
Schneider et al., "Activation of retinoic acid receptor alpha is sufficient for full induction of retinoid responses in SK-BR-3 and T47D human breast cancer cells," Cancer Res. 60(19):5479-87 (2000).
Japanese Office Action with English translation for Japanese Patent Application No. 2013-527250, mailed Jul. 30, 2015 (6 pages).
Certified English translation of Japanese Patent Application No. 2005-206544 (14 pages).

* cited by examiner

PALOVAROTENE

4-[(1E)-2-[5,6,7,8-Tetrahydro-
5,5,8,8-tetramethyl-3-(1Hpyrazol-
1-ylmethyl)-2-
naphthalenyl]ethenyl]benzoic acid

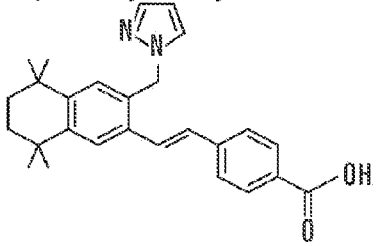

CD 1530
Cat No. 2554

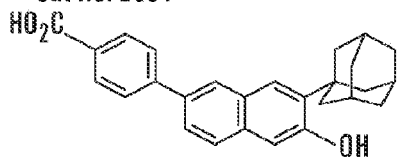

CHEMICAL NAME: 4-(6-Hydroxy-7-tricyclo
[3.3.1.13,7]dec-1-yl-2-naphthale nyl)benzoic acid CD 437
Cat No. 1549

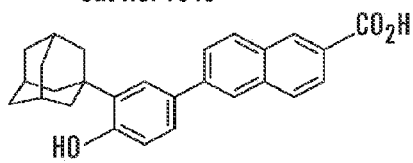

ALTERNATIVE NAME: AHPN
CHEMICAL NAME: 6-(4-Hydroxy-3-tricyclo
[3.3.1.13,7]dec-1-ylphenyl)
-2-na phthatelenecarboxylic acid

BMS 270394
(R)-(+)-BMS-270394

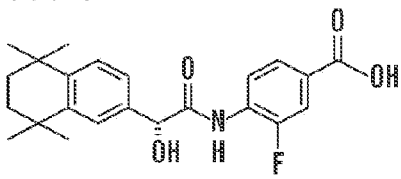

CAS 262433-54-5
C23H26FNO4 MW 399.47

BMS270394 WAS PURCHASED FROM AXON.
CD437 AND CD1530 WERE PURCHASED FROM TOCRIS USA
PALAVAROTENE (RG67) WAS PURCHASED FROM ATOMAX CHEMICALS CO., LTD.

*FIG. 3*

COMPOSITION AND METHOD FOR MUSCLE REPAIR AND REGENERATION

RELATED APPLICATIONS

This application is a continuation of U.S. Ser. No. 13/819,914, which has a 371(c) date of May 15, 2013, which is a 35 U.S.C. §371 National Phase Entry Application of International Application No. PCT/US2011/049905 filed Aug. 31, 2011, which designates the U.S., and which claims benefit under 35 U.S.C. §119 (e) of U.S. Provisional Application Ser. No. 61/378,996, filed Sep. 1, 2010, the contents of each of which are incorporated herein by reference in their entirety.

GOVERNMENT SUPPORT

This invention was made with government support under Grant No. W81XWH-07-1-0212 awarded by the United States Army. The government has certain rights in this invention.

FIELD OF THE INVENTION

The present invention relates to methods and compositions for muscle repair and regeneration.

BACKGROUND OF THE INVENTION

Injuries to muscles include acute injuries to skeletal muscles such as contusions (bruises), lacerations, ischemia, strains, and complete ruptures. These injuries may cause tremendous pain and can incapacitate the affected person, preventing them from being able to go to work or even to participate in normal daily activities.

Skeletal muscles can become injured for a variety of reasons including over-use, trauma, infections and loss of blood circulation. In general, muscles have adequate repair capacity particularly in young people, but this repair process can become ineffective in older people or after repeated rounds of over-use, severe trauma or other processes. In such cases, the muscles lose function and strength of contraction and can be replaced by scar tissue (connective tissue) that by lacking contractility, causes loss of muscle function. Current therapies include massage, ultrasound, hyperbaric oxygen delivery, and drug treatments such as fenoterol and insulin-like growth factor-1. These therapies can provide some beneficial outcomes, but are far from ideal in terms of effectiveness and efficiency. In addition, current therapies are not specifically directed toward basic mechanisms of muscle cell repair and regeneration.

Accordingly, there exists a need for methods and compositions that can induce muscle repair and regeneration speedily and effectively.

SUMMARY OF THE INVENTION

In one aspect, the invention provides a method for muscle repair or regeneration in a subject, the method comprising administering a therapeutically effective amount of a retinoic acid receptor (RAR) agonist to a subject, which subject has a damaged muscle tissue. In some embodiments, the RAR agonist is a RARγ agonist.

One aspect of the invention relates to a method of muscle repair or regeneration in a subject, comprising administering a therapeutically effective amount of a retinoic acid receptor gamma (RARγ) agonist to a subject with damaged muscle tissue, to thereby repair or regenerate the damaged muscle tissue. In one embodiment of the methods described herein, the administration is local or systemic. In one embodiment of the methods described herein, administration is begun during a time period of increased endogenous retinoid signaling in the subject resulting from incurrence of the damaged muscle tissue. In one embodiment of the methods described herein, administration is begun later than 3 days after incurrence of the damaged muscle tissue by the subject. In one embodiment of the methods described herein, administration is begun at about 4 days after incurrence of the damaged muscle tissue by the subject. In one embodiment of the methods described herein, administration is begun at about 5 days after incurrence of the damaged muscle tissue by the subject. In one embodiment of the methods described herein, administration is begun at about 6 days after incurrence of the damaged muscle tissue by the subject. In one embodiment of the methods described herein, administration is begun at about 7 days after incurrence of the damaged muscle tissue by the subject. In one embodiment of the methods described herein, administration is begun at about 5 days, and is continued through to at least day 7 after incurrence of the damaged muscle tissue by the subject. In one embodiment of the methods described herein, administration is continued through to at least day 9 after incurrence of the damaged muscle tissue by the subject. In one embodiment of the methods described herein, the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthalenyl)benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy)phenyl]naphthalene-2-carboxylic acid; 5-[(E)-3-oxo-3-(5,5,8,8-tetrahydronaphthalene-2-yl)propenyl]thiophene-2-carboxylic acid; and enantiomers, derivatives, prodrugs, and pharmaceutically acceptable salts thereof. In one embodiment of the methods described herein, the damaged muscle tissue is the result of a physical injury or accident, disease, infection, over-use, loss of blood circulation, or muscle atrophy or wasting. In one embodiment of the methods described herein, the damaged muscle tissue is dystrophic muscle or an ageing muscle. In one embodiment of the methods described herein, the damaged muscle tissue is the result of muscle atrophy/wasting. In one embodiment of the methods described herein, the subject is a mammal. In one embodiment of the methods described herein, the subject is a mouse. In one embodiment of the methods described herein, the subject is human. In one embodiment of the methods described herein, the method further comprises administering an anti-inflammatory agent to the subject.

Another aspect of the present invention relates to a method of muscle repair or regeneration in a subject, comprising administering pluripotent or multipotent stem cells that have been pre-treated with a RARγ agonist, to a subject at a site of muscle injury, to thereby repair or regenerate muscle at the site. In one embodiment of the methods described herein, the muscle injury is a compound tissue injury. In one embodiment of the methods described herein the compound tissue injury comprises an injury to muscle and bone. In one embodiment of the methods described herein the pre-treated stem cells are administered in combination with non-treated stem cells. In one embodiment of the methods described herein the pre-treated stem cells and non-treated stem cells are administered at a ratio of 1:1. In one embodiment of the methods described herein, the pre-treated stem cells have been pre-treated with the RARγ agonist for a period of about 3 days. In one embodiment of the methods described herein, the pluripotent stem cells are induced pluripotent stem cells. In one embodiment of the methods described herein, the pluripotent stem cells are mesenchymal stem cells. In one embodiment of the methods described herein, administering is local. In one embodiment of the methods described herein, administering is by transplantation of the cells into the subject. In one embodiment of the methods described herein, the pluripotent stem cells are autologous or heterologous to the subject. In one embodiment of the methods described herein, the pluripotent stem cells are mammalian. In one embodiment of the methods described herein, the pluripotent stem cells are rodent. In one embodiment of the methods described herein, the pluripotent stem cells are human. In one embodiment of the methods described herein, the method further comprises administering an anti-inflammatory agent to the subject. In one embodiment of the methods described herein, the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-ricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthale nyl)benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]benzoic acid) BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-yny loxy)phenyl]naphthalene-2-carboxylic acid; 5-[(E)-3-oxo-3-(5,5,8,8-tetrahydronaphthalene-2-yl)propenyl]thiophene-2-carboxylic acid; and enantiomers, derivatives, prodrugs, pharmaceutically acceptable salts thereof, and combinations thereof. In one embodiment of the methods described herein, the injured muscle results from physical injury or accident, disease, infection, over-use, loss of blood circulation, or muscle atrophy or wasting. In one embodiment of the methods described herein, the injured muscle tissue is dystrophic muscle or an ageing muscle. In one embodiment of the methods described herein, the injured muscle is the result of muscle atrophy/wasting.

Another aspect of the invention relates to a method of inducing or stimulating myogenic differentiation of isolated mesencymal stem cells in vitro comprising, contacting the mesencymal stem cells with an effective amount of a retinoic acid receptor gamma (RARγ) agonist. In one embodiment of the methods described herein, contacting is for a time period selected from the group consisting of about 12 hours, about 1 day, about 2 days, and about 3 days.

Another aspect of the invention relates to a method of inducing or stimulating lineage-directed differentiation of a pluripotent stem cell into a mesenchymal lineage, the method comprising contacting the pluripotent stem cell with an effective amount of a retinoic acid receptor gamma (RARγ) agonist. In one embodiment of the methods described herein, the pluripotent stem cell is an induced pluripotent stem cell. In one embodiment of the methods described herein, the pluripotent stem cell is a mesenchymal stem cell. In one embodiment of the methods described herein, the mesenchymal lineage is selected from the group consisting of myogenic, osteogenic, chodrogenic, tendonogenic, ligamentogenic, maroow stromagenic, adipogenic, and dermogenic. In one embodiment of the methods described herein, the pluripotent stem cell is mammalian. In one embodiment of the methods described herein, the pluripotent stem cell is rodent. In one embodiment of the methods described herein, the pluripotent stem cell is human. In one embodiment of the methods described herein, the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthalenyl)benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy -2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy)phenyl]naphthalene-2-carboxylic acid; 5-[(E)-3-oxo-3-(5,5,8,8-tetrahydronaphthalene-2-yl)propenyl]thiophene-2-carboxylic acid; and enantiomers, derivatives, prodrugs, pharmaceutically acceptable salts thereof, and combinations thereof.

Another aspect of the invention relates to a composition comprising a mesenchymal stem cells wherein a portion of the mesenchymal stem cells have been pretreated by contact with a RARγ agonist to thereby generate pretreated mesenchymal stem cells. In one embodiment of the compositions described herein, the portion of pretreated mesenchymal stem cells is selected from the group consisting of 10%, 20%, 30%, 40%, 50%, 60%, 70%, 80%, and 90%.

Another aspect of the invention relates to a composition comprising a pluripotent stem cell population, wherein at least one cell of the population was contacted with a RARγ agonist to thereby generate a pretreated pluripotent stem cell. In one embodiment of the compositions described herein, the pluripotent stem cell is an induced pluripotent cell. In one embodiment of the compositions described herein, the pluripotent stem cell is a mesenchymal stem cell. In one embodiment of the compositions described herein, the stem cell is an isolated stem cell. In one embodiment of the compositions described herein, the stem cell is mammalian. In one embodiment of the compositions described herein, the stem cell is murine. In one embodiment of the compositions described herein, the stem cell is human. In one embodiment of the compositions described herein, the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthalenyl)benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-

(adamantan-1-yl)-4-(prop-2-ynyloxy)phenyl]naphthalene-2-carboxylic acid; 5-[(E)-3-oxo-3-(5,5,8,8-tetrahydronaphthalene-2-yl)propenyl]thiophene-2-carboxylic acid; and enantiomers, derivatives, prodrugs, pharmaceutically acceptable salts thereof, and combinations thereof.

Another aspect of the present invention relates to a pharmaceutical composition comprising a composition comprising a pluripotent stem cell populations described herein and a pharmaceutically acceptable carrier.

Another aspect of the present invention relates to a kit for repairing or regenerating muscle, comprising at least one of a RARγ agonist, a RARγ agonist and a stem cell, or a composition comprising a stem cell, described herein. In one embodiment of the kits described herein, the stem cell is an induced pluripotent stem cell. In one embodiment of the kits described herein, the stem cell is a mesenchymal stem cell. In one embodiment of the kits described herein, the RARγ agonist is formulated in a pharmaceutical composition. In one embodiment of the kits described herein, the RARγ agonist is formulated for topical application. In one embodiment of the kits described herein, the stem cell is an isolated stem cell. In one embodiment of the kits described herein, the stem cell is mammalian. In one embodiment of the kits described herein, the stem cell is rodent. In one embodiment of the kits described herein, the stem cell is human. In one embodiment of the kits described herein, the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthalenyl)benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy)phenyl]naphthalene-2-carboxylic acid; 5-[(E)-3-oxo-3-(5,5,8,8-tetrahydronaphthalene-2-yl)propenyl]thiophene-2-carboxylic acid; and enantiomers, derivatives, prodrugs, pharmaceutically acceptable salts thereof, and combinations thereof. In one embodiment of the kits described herein, the kit further comprises instructions for use.

BRIEF DESCRIPTION OF THE DRAWINGS

FIG. 3 are names and chemical structures of some exemplary RARγ agonists.

DETAILED DESCRIPTION OF THE INVENTION

Figure 1:
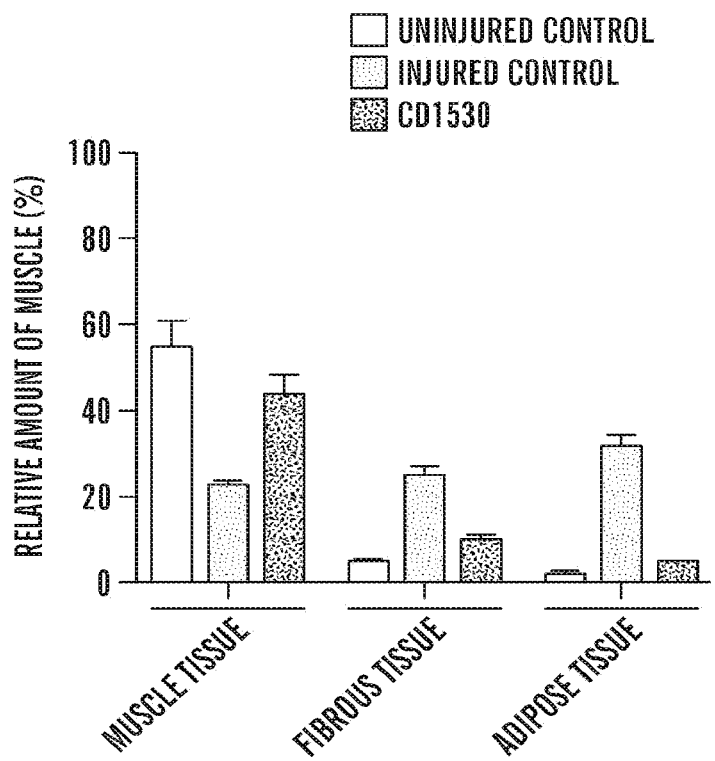
FIG. 1 is a bar graph of data obtained from the histological analysis of skeletal muscle tissue 4-week after injury. To evaluate and quantify the changes of skeletal muscle tissue structure, images of trichrome-stained serial sections were taken and used to determine the relative amounts of muscle fiber, adipose and fibrous tissues in multiple defined areas by ImagePro software. The analyzed areas were 9×9 grids each (about 3×3 mm) that included the original injured site (2×2 mm). Note that muscle injury caused a decrease in total muscle fiber area and a concurrent increase in fibrous and adipose tissues area. In contrast, CD1530 treatment largely restored the tissue composition.

Aspects of the invention relate to the finding that progenitor stem cells can be induced to undergo muscle differentiation by acute or chronic exposure to retinoic acid receptor gamma (RARγ) agonists. Accordingly, in one aspect, the invention provides a method for repairing or regenerating a damaged muscle tissue of a subject, the method comprising administering a therapeutically effective amount of a retinoic acid receptor (RAR) agonist to a subject, which subject has a damaged muscle tissue.

As used herein, the term "damaged muscle tissue" refers to a muscle tissue, such as a skeletal or cardiac muscle that has been altered for instance by a physical injury or accident, disease, infection, over-use, loss of blood circulation, or by genetic or environmental factors. A damaged muscle tissue can be a dystrophic muscle or an ageing muscle. Exemplary symptoms of muscle damage include, but are not limited to, swelling, bruising or redness, open cuts as a consequence of an injury, pain at rest, pain when specific muscle or the joint in relation to that muscle is used, weakness of the muscle or tendons, and an inability to use the muscle at all.

In some embodiments of this and other aspects of the invention, the damaged muscle tissue results from muscle atrophy/wasting. In some embodiments of this and other aspects of the invention, the damaged muscle tissue results from a physical injury.

In some embodiments of this and other aspects of the invention, the damaged muscle is skeletal muscle.

In some embodiments of this and other aspects of the invention, disease resulting in damaged muscle tissue is a myopathy. Without limitation, myopathy can be a congenital myopathy or an acquired myopathy. Exemplary myopathies include, but are not limited to, dystrophies, myotonia (neuromytonia), congenital myopathies (e.g., nemaline myopathy, multi/minicore myopathy, centronuclear myopathy (or myotubular myopathy)), mitochondrial myopathies, familial periodic paralysis, inflammatory myopathies, metabolic myopathies (e.g., glycogen storage disease and lipid storage disorder), dermatomyositis, polymyositis inclusion body myositis, myositis ossificans, rhabdomyolysis and myoglobinuirias.

In some embodiments of this and other aspects of the invention, myopathy is a dystrophy selected from the group consisting of muscular dystrophy, Duchenne muscular dystrophy, Becker's muscular dystrophy, Reflex sympathetic dystrophy, Retinal dystrophy, Conal dystrophy, Myotonic dystrophy, Corneal dystrophy, and any combinations thereof.

Without wishing to be bound by a theory, methods described herein reduce and/or inhibit formation of scar-like tissue in the damaged muscle tissue. Accordingly, in some embodiments, formation of scar-like tissue formation in the damaged muscle tissue is reduced by at least 5%, at least 10%, at least 20%, at least 30%, at least 40%, at least 50%, at least 60%, at least 70%, at least 80%, at least 90%, at least 95%, or 100% (complete reduction) relative to a reference level.

In some embodiments, amount of adipose tissue and/or connective tissue in the damaged muscle tissue is reduced by at least 5%, at least 10%, at least 20%, at least 30%, at least 40%, at least 50%, at least 60%, at least 70%, at least 80%, at least 90%, at least 95%, or 100% (completer reduction) relative to a reference level.

Again, without wishing to be bound by a theory, the methods described herein lead to an increase in the amount of myosin heavy chain (MHC) in the damaged muscle tissue. Accordingly, in some embodiments amount of myosin heavy chain (MHC) in the damaged muscle tissue in increased by at least 5%, at least 10%, at least 20%, at least 30%, at least 40%, at least 50%, at least 60%, at least 70%, at least 80%, at least 90%, at least, 1-fold, 2-fold, 3-fold, 4-fold, 5-fold, 10-fold, 50-fold, or 100-fold or more, relative to reference level.

Additionally, the methods described herein increase the number of MHC positive elongated muscle-like cells. Accordingly, in some embodiments, number of MHC positive elongated muscle-like cells in the damaged muscle tissue is increased by at least 5%, at least 10%, at least 20%, at least 30%, at least 40%, at least 50%, at least 60%, at least 70%, at least 80%, at least 90%, at least, 1-fold, 2-fold, 3-fold, 4-fold, 5-fold, 10-fold, 50-fold, or 100-fold or more, relative to reference level.

As discussed herein, progenitor stem cells can be induced or stimulated to undergo muscle differentiation by acute or chronic exposure to retinoic acid receptor gamma (RARγ) agonists. Accordingly, an increase in myogenic regulatory factors is observed. Myogenic regulatory factors are basic-helix-loop-helix (bHLH) transcription factors that regulate myogenesis. See for example, Perry, R. & Rudnick, M. (2000). "Molecular mechanisms regulating myogenic determination and differentiation", *Front Biosci* 5: D750-67 (2000), content of which is herein incorporated by reference. Exemplary myogenic regulatory factors include, but are not limited to, MyoD (Myf3), Myf5, myogenin, and MRF4 (Myf6). MyoD is one of the earliest markers of myogenic commitment. MyoD is expressed in activated satellite cells, but not in quiescent satellite cells. Although MyoD marks myoblast commitment, muscle development is not dramatically ablated in mouse mutants lacking the MyoD gene. This is likely to be due to functional redundancy from Myf5.

Accordingly, in some embodiments, level of at least one myogenic regulatory factor in the damaged muscle tissue increases by at least 5%, at least 10%, at least 20%, at least 30%, at least 40%, at least 50%, at least 60%, at least 70%, at least 80%, at least 90%, at least, 1-fold, 2-fold, 3-fold, 4-fold, 5-fold, 10-fold, 50-fold, or 100-fold or more, relative to reference level.

In some embodiments, amount of at least one laminin in the damaged muscle tissue is increased by at least 5%, at least 10%, at least 20%, at least 30%, at least 40%, at least 50%, at least 60%, at least 70%, at least 80%, at least 90%, at least, 1-fold, 2-fold, 3-fold, 4-fold, 5-fold, 10-fold, 50-fold, or 100-fold or more, relative to reference level.

Retinoic Acid Receptor (RAR) Agonists

As used herein, the term "RAR agonist" is any compound that is capable of transactivating any of the retinoic acid receptor with an ED50 of less than 1000 nM, less than 500 nM, less than 250 nM, less than 200 nM, less than 100 nM, less than 50 nM, less than 25 nM, less than 20 nM, less than 10 nM, less than 1 nM, less than 0.1 nM, less than 0.01 nM, or less than 0.001 nM.

The retinoid receptors are classified into two families, the retinoic acid receptors (RARs) and the retinoid X receptors (RXRs), each consisting of three distinct subtypes α, β, and γ. Each subtype of the RAR gene family encodes a variable number of isoforms arising from differential splicing of two primary RNA transcripts. All-trans retinoic acid (ATRA) and its other naturally occurring retinoid analogs (9-cis retinioc acid, all-trans 3-4 didehydro retinioc acid, 4-oxo retinoic acid and retinol) are pleiotrophic regulatory compounds that bind with retinoid receptors. For example, ATRA binds with approximately equal affinity to all the three RAR subtypesm, but does not bind to the RXR receptors. Instead, for these receptors, 9-cis retinoic acid is the natural ligand.

As used herein, the term "transactivation" refers to the ability of an RAR agonist to activate the transcription of a gene where the gene transcription is initiated by the binding of a ligand to the particular retinoic acid receptor being tested, i.e., RARα, RARβ, or RARγ. Determining the ability of a compound to transactivate a retinoic acid receptor may be performed by methods known to those of skill in the art. Examples of such methods are found in Bernard et al., Biochem. Biophys. Res. Commun, 186: 977-983 (1992) and Apfel et al., Proc. Nat. Sci. Acad. (USA), 89: 7129-7133 (1992), content of both of which is herein incorporated by reference.

In some embodiments of the aspects described herein, the RAR agonist is a RARγ selective agonist. As used herein, the term "RARγ selective agonist" refers to a compound that is able to selectively bind to the RARγ receptor and promote RARγ activation. Generally, RARγ selective agonists will bind to the RARγ receptor at significantly lower concentrations than the RARα and RARβ receptors. For example, a RARγ selective agonist will bind to the RARγ receptor with a more than 5-fold, more than 10-fold, more than 20-fold, more than 30-fold, more than 40-fold, more than 50-fold, more than 60-fold, more than 70-fold, more than 80-fold, more than 90-fold or more selectivity, than the RARα and RARβ receptors.

The RARγ agonist selectivity of a compound can be determined by routine ligand binding assays known to one of skill in the art such as described in Apfel et al., Proc. Nat. Sci. Acad. (USA), 89: 7129-7133 (1992); M. Teng et al., J. Med. Chem., 40: 2445-2451 (1997); and PCT Pub. No. WO1996/30009, content of all of which is herein incorporated by reference.

In some embodiments of the aspects described herein, the RAR agonist is a RARγ/β selective agonist. As used herein, the term "RARγ/β selective agonist" refers to a compound that selectively binds to RARγ and RARβ receptors, promoting both RARγ and RARβ activation and sparing the activation of RARα receptors.

In some embodiments of the aspects described herein, the RAR agonist is a RAR agonist that is at least gamma selective and is RARα sparing. As used herein, the term "RAR agonist that is at least gamma selective and is RARα sparing" refers to a compound that is RARγ selective or RARγ/β selective.

In some embodiments of the aspects described herein, the RAR agonist is a RAR pan agonist. As used herein, the term "RAR pan agonist" refers to a compound that binds to RARα, RARβ, and RARγ receptors with similar affinity, promoting RARα, RARβ, and RARγ activation.

Exemplary, RAR agonists include, but are not limited to, CD-271 (6-(4-Methoxy-3-tricyclo[3.3.1.13,7]dec-1-ylphenyl)-2-naphthalenecarboxylic acid); CD-394, CD-437 (6-(4-

Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthalenyl)benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy)phenyl]naphthalene-2-carboxylic acid; 5-[(E)-3-oxo-3-(5,5,8,8-tetrahydronaphthalene-2-yl)propenyl]thiophene-2-carboxylic acid; and enantiomers, derivatives, prodrugs, and pharmaceutically acceptable salts thereof.

Other RAR agonists amenable to the present invention are described, for example, in U.S. Pat. No. 5,624,957; U.S. Pat. No. 5,760,084; U.S. Pat. No. 6,331,570; U.S. Pat. No. 6,300,350; U.S. Pat. No. 5,700,836; No. 5,726,191; U.S. Pat. No. 5,498,795; U.S. Pat. No. 5,130,335; Int. Pat. App. Pub. No. WO1997/037648, No. WO2007/068579, and No. WO2007/068580; French Pat. App. No. FR2739557 published Apr. 11, 1997; and Japanese Pat. Pub. No. 62/053981, content of all which is herein incorporated by reference in its entirety. Further RAR agonists amenable to the present invention include those described in Biochem. Biophys. Res. Commun. 179: 1554-1561 (1992), Biochem. Biophys. Res. Commun 186: 977-984 (1992), Int. J. Cancer 71: 497 (1997), Skin Pharmacol. 8: 292-299 (1995), J. Med. Chem. 39: 2411-2421 (1996), Cancer Res. 55: 4446-4451 (1995), Cancer Letters 115: 1-7 (1997), J. Med. Chem. 32: 834-840 (1989), content of all of which is herein incorporated by reference.

Pharmaceutically Acceptable Salts

As used herein, the term "pharmaceutically-acceptable salts" refers to the conventional nontoxic salts or quaternary ammonium salts of the RAR agonists, e.g., from non-toxic organic or inorganic acids. These salts can be prepared in situ in the administration vehicle or the dosage form manufacturing process, or by separately reacting a purified RAR agonist in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Prodrugs

As used herein, a "prodrug" refers to compounds that can be converted via some chemical or physiological process (e.g., enzymatic processes and metabolic hydrolysis) to a RAR agonist. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3): 63-80 (1999); Waller et al., "Prodrugs", *Br. J. Clin. Pharmac.* 28: 497-507 (1989), content of all of which is herein incorporated by reference in its entirety.

Pharmaceutical Compositions

For administration to a subject, the RAR agonists can be provided in pharmaceutically acceptable compositions. These pharmaceutically acceptable compositions comprise a therapeutically-effective amount of one or more of the RAR agonists, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773, 919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "effective-amount" as used herein, refers to an amount of an active agent (e.g., an RARγ agonist) sufficient to produce the desired change or effect (e.g., priming mesenchymal stem cells toward myogenic differentiation in vitro).

The phrase "therapeutically-effective amount" as used herein means that amount of a compound, material, or composition comprising a RAR agonist which is effective for producing some desired therapeutic effect in at least a sub-population of cells in an animal at a reasonable benefit/risk ratio applicable to any medical treatment. For example, an amount of a RARγ agonist administered to a subject that is sufficient to produce a statistically significant, measurable muscle repair or regeneration.

As used herein, the term "repair" refers to a process by which the damages of a muscle tissue are alleviated or completely eliminated. In some embodiments, at least one symptom of muscle tissue damage is alleviated by at least 5%, at least 10%, at least 20%, at least 30%, at least 40%, or at least 50%. Symptoms of muscle damage are described, for example, in "Skeletal Muscle Damage and Repair" Tiidus, P. M., ed., Human Kinetics (2008), content of which is herein incorporated by reference.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more RAR agonist (or RAR agonist treated cells) being delivered to a specific location as compared to the entire body of the subject, whereas, systemic administration results in delivery of a RAR agonist (or RAR agonist treated cells) to essentially the entire body of the subject. One method of local administration is by intramuscular injection.

In the context of administering a RAR agonist treated cell, the term "administering" also include transplantation of such a cell into a subject. As used herein, the term "transplantation" refers to the process of implanting or transferring at least one cell into a subject. The term "transplantation" includes, e.g., autotransplantation (removal and transfer of cell(s) from one location on a patient to the same or another location on the same patient), allotransplantation (transplantation between members of the same species), and xenotransplantation (transplantations between members of different species). Skilled artisan is well aware of methods for implanting or transplantation of mesenchymal stem cells for muscle repair and regeneration, which are amenable to the present invention. See for example, U.S. Pat. No. 7,592,174 and U.S. Pat. Pub. No. 2005/0249731, content of both of which is herein incorporated by reference.

Furthermore, the RAR agonist can be formulated in the form of ointments, creams powders, or other formulations suitable for topical formulations. Because the molecular weight of RAR agonists is generally less than 500 daltons, these formulations can deliver the agonist from skin to deeper muscle tissue. Accordingly, such formulations may comprise one or more agents that enhance penetration of active ingredient through skin. For topical applications, the RAR agonist can be included in wound dressings and/or skin coating compositions.

A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments of the aspects described herein, the compositions are administered by intravenous infusion or injection.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used to treat domesticated animals and/or pets.

A subject can be one who has been previously diagnosed with or identified as suffering from or having a disorder characterized with muscle damage or muscle atrophy/wasting.

A subject can be one who is not currently being treated with a RAR agonist.

A subject can be one who has been previously diagnosed with a disease that is being treated with a therapeutic regime comprising a RAR agonist, wherein the disease is not a disease characterized with muscle damage or muscle atrophy/wasting Accordingly, in some embodiments, the treatment method comprising adjusting the therapeutic regime of the subject such that at least one symptom of muscle damage is reduced. Without limitation, a therapeutic regime can be adjusted by modulating the frequency of administration of the RAR and/or by altering the site or mode of administration.

In some embodiments of the aspects described herein, the method further comprising diagnosing a subject for muscle damage or muscle atrophy/wasting before treating the subject for muscle repair or regeneration.

In some embodiments of the aspects described herein, the method further comprising selecting a subject with muscle damage or muscle atrophy/wasting before treating the subject for muscle repair or regeneration.

Combination Therapy

In some embodiments of the aspects described herein, the RAR agonist is administered to the subject along with a therapy selected from massage, ultrasound, hyperbaric oxygen delivery. In addition, and/or alternatively, the RAR agonist can be administrated to a subject in combination with a pharmaceutically active agent. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

In some embodiments of the aspects described herein, the pharmaceutically active agent include those agents known in the art for treatment of inflammation or inflammation associated disorders, or infections. Exemplary anti-inflammatory agents include, but are not limited to, non-steroidal anti-inflammatory drugs (NSAIDs—such as aspirin, ibuprofen, or naproxen, coricosteroids (such as presnisone), anti-malarial medication (such as hydrochloroquine), methotrexrate, sulfasalazine, leflunomide, anti-TNF medications, cyclophosphamise and mycophenolate.

In some embodiments of the aspects described herein, the pharmaceutically active agent is a growth factor. Exemplary growth factors include, but are not limited to, fibroblast growth factors (FGF), FGF-1, FGF-2, FGF-4, thymosins, platelet-derived growth factors (PDGF), insulin binding growth factors (IGF), IGF-1, IGF-2, epidermal growth factor (EGF), transforming growth factor (TGF), TGF-.alpha., TGF-.beta., cartilage inducing factors-A and -B, osteoid-inducing factors, osteogenin, bone morphogenic proteins, and other bone growth factors, collagen growth factors, heparin-binding growth factor-1 or -2, and their biologically active derivatives.

In some embodiments of the aspects described herein, the pharmaceutically active agent is an anti-interferon agent. Without limitation, anti-interferon agents include anti-interferon antibodies or fragments or derivatives thereof. Exemplary anti-interferon antibodies include, but are not limited to, those described in Ronnblom, L. & Elkon, K. B. Cytokines as therapeutic targets in SLE. Nat Rev Rheumatol 6, 339-647; Yao, Y. et al. Neutralization of interferon-alpha/beta-inducible genes and downstream effect in a phase I trial of an anti-interferon-alpha monoclonal antibody in systemic lupus erythematosus. *Arthritis Rheum* 60, 1785-96 (2009); and Zagury, D. et al. IFNalpha kinoid vaccine-induced neutralizing antibodies prevent clinical manifestations in a lupus flare murine model. *Proc Natl Acad Sci USA* 106, 5294-9 (2009), those described in U.S. Pat. No. 4,902,618; U.S. Pat. No. 5,055,289; U.S. Pat. No. 7,087,726; and No. 7,741,449, and those described in U.S. Pat. App. Pub. No. 10/440,202; No. 11/342,020; and No. 12/517,334, content of all of which is herein incorporated by reference.

In some embodiments of the aspects described herein, the pharmaceutically active agent is fenoterol or insulin-like growth factor-1.

The RAR agonist and the pharmaceutically active agent can be administrated to the subject in the same pharmaceutical composition or in different pharmaceutical compositions (at the same time or at different times). When administered at different times, the RARγ agonist and the pharmaceutically active agent can be administered within 5 minutes, 10 minutes, 20 minutes, 60 minutes, 2 hours, 3 hours, 4, hours, 8 hours, 12 hours, 24 hours of administration of the other. When the RAR agonist and the pharmaceutically active agent are administered in different pharmaceutical compositions, routes of administration can be different.

Dosage

The amount of RAR agonist that can be combined with a carrier material to produce a single dosage form will generally be that amount of the RAR agonist that produces a therapeutic effect. Generally out of one hundred percent, this amount will range from about 0.01% to 99% of RAR agonist, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that RARγ agonist is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that RAR agonist or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the RAR agonist. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such subdoses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In one embodiment, administration of the RAR agonist to the subject in the methods described herein is at one or more times. In one embodiment, one time of administration, or a plurality of times of the administration, are within a time period of detectable increased endogenous retinoid signaling that occurs naturally in vivo in response to the damage (e.g, an incurred trauma or physiological change that leads to muscle damage) to the muscle tissue (e.g., by day 4 or day 5 after the incurrence of the damage). In one embodiment, administration includes a time that is at the beginning of the time period. In one embodiment, administration includes several times that are within the time period. In one embodiment, administration is at or includes a time that is after a period of time that is greater than 3 days after incurrence of the damage. In one embodiment, administration is at or includes a time that is about 4 days after incurrence of the damage. In one embodiment, administration is at or includes a time that is at about 5 days after incurrence of the damage. In one embodiment, administration is at or includes a time that is at about 6 days after incurrence of the damage. In one embodiment, administration is at or includes a time that is at about 7, or about 8 days after incurrence of the damage. Combinations of these times of administration are also envisioned. For example, administration at about day 4, and then one or more of days 5, 6, 7, and 8. In one embodiment, administration is at about day 5 and day 7. Continued administration over an extended period of time (e.g., until satisfactory recovery is obtained) can also be performed.

In one embodiment, the administration overlaps with or encompasses the time period of increased endogenous retinoid signaling (e.g., administration begins prior to the increased endogenous retinoid signaling, and extends into and/or throughout this period). In one embodiment, the administration is withheld until the increased endogenous retinoid signaling in response to the damage to the muscle tissue (e.g. administration begins following day 3, or at day 4, 5, 6, 7, 8, or 9 or later). In one embodiment, administration begins following day 3 (e.g., day 4 or 5), and is continued through to at least day 9 (e.g., until day 11). In one embodiment, administration is every day or every other day during the recited time periods of administration. In one embodiment, administration is at least on day 5, 7, and 9.

Pre-Treated Stem Cells

In another aspect, the invention provides a population of stem cells, wherein the population is produced by contacting at least one cell stem cell with an effective amount of a RAR agonist. As used herein, the term "population of stem cells" means one or more stem cells. Such stem cells can be isolated, (e.g., for contacting in vitro, or ex vivo). Such contacting enables the cells to regenerate muscle tissue and also to support myogenic differentiation of other cells (e.g., cells in a host into which the pre-treated cells are administered). In one embodiment, the contact is with RARγ agonist, to isolated mesenchymal stem cells, to enable this ability. In one embodiment, pre-treatment is in vitro and is for at least about 3 days. Although shorter periods of pre-treatment (e.g., 2.5 days, 2 days, 1.5 days, 1 day, 12 hours) may also produce similar abilities. Such pre-treated cells which are thus induced, are referred to herein as "pre-treated". All pre-treated cells described herein are encompassed by the present invention.

The term "contacting" or "contact" as used herein in connection with contacting a stem cell includes subjecting the stem cell to an appropriate culture media which comprises a RAR agonist. The stem cell can be contacted with an RAR agonist in a cell culture, e.g., in vitro or ex vivo. As used herein, the term "ex vivo" refers to cells which are removed from a living organism and cultured outside the organism (e.g., in a test tube). Ex vivo cells can then be administered upon modification to the donor.

In some embodiments of the aspects of the invention, the stem cell is a human stem cell. In some embodiments, the stem cell is a pluripotent or multipotent stem cell. In some embodiments, the stem cell is an induced pluripotent stem (iPS) cell, or a stably reprogrammed cell which is an intermediate pluripotent stem cell and can be further reprogrammed into an iPS cell, e.g., partial induced pluripotent stem cells (also referred to as "piPS cells"). In some embodiments, the pluripotent stem cell, iPSC or piPSC is a genetically modified pluripotent stem cell. In some embodiments, the stem cell is a mesenchymal stem cell.

Generally, a stem cell for use in the methods, assays, systems, kits and to generate scorecards can be obtained or derived from any available source. Accordingly, a stem cell can be obtained or derived from a vertebrate or invertebrate. In some embodiments of this and other aspects of the invention, the stem cell is a mammalian stem cell.

In some embodiments of this and other aspects of the invention, the stem cell is a primate or a rodent stem cell.

In some embodiments of the aspects of the invention, the stem cell is selected from the group consisting of chimpanzee, cynomologous monkey, spider monkey, macaques (e.g. Rhesus monkey), mouse, rat, woodchuck, ferret, rabbit, hamster, cow, horse, pig, deer, bison, buffalo, feline (e.g., domestic cat), canine (e.g. dog, fox and wolf), avian (e.g. chicken, emu, and ostrich), and fish (e.g., trout, catfish and salmon) stem cell.

As used herein, the term "differentiation" as used herein refers to the cellular development of a cell from a primitive stage towards a more mature (i.e. less primitive) cell.

As used here in, the term "induced pluripotent stem cell" or "iPSC" or "iPS cell" refers to a cell derived from a complete reversion or reprogramming of the differentiation state of a differentiated cell (e.g. a somatic cell). As used herein, an iPSC is fully reprogrammed and is a cell which has undergone complete epigenetic reprogramming.

The term "reprogramming" as used herein refers to a process that alters or reverses the differentiation state of a differentiated cell (e.g. a somatic cell). Stated another way, reprogramming refers to a process of driving the differentiation of a cell backwards to a more undifferentiated or more primitive type of cell. Complete reprogramming involves complete reversal of at least some of the heritable patterns of nucleic acid modification (e.g., methylation), chromatin condensation, epigenetic changes, genomic imprinting, etc., that occur during cellular differentiation as a zygote develops into an adult. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods of the invention may also be of use for such purposes.

The term "stable reprogrammed cell" as used herein refers to a cell which is produced from the partial or incomplete reprogramming of a differentiated cell (e.g. a somatic cell). A stable reprogrammed cell is used interchangeably herein with "piPSC". A stable reprogrammed cell has not undergone complete reprogramming and thus has not had global remodeling of the epigenome of the cell. A stable reprogrammed cell is a pluripotent stem cell and can be further reprogrammed to an iPSC, as that term is defined herein, or alternatively can be differentiated along different lineages. In some embodiments, a partially reprogrammed cell expresses markers from all three embryonic germ layers (i.e. all three layers of endoderm, mesoderm or ectoderm layers). Markers of endoderm cells include, Gata4, FoxA2, PDX1, Nodal, Sox7 and Sox17. Markers of mesoderm cells include, Brachycury, GSC, LEF1, Mox1 and Tie1. Markers of ectoderm cells include cripto1, EN1, GFAP, Islet 1, LIM1 and Nestin. In some embodiments, a partially reprogrammed cell is an undifferentiated cell.

The term "remodeling of the epigenome" refers to chemical modifications of the genome which do not change the genomic sequence or a gene's sequence of base pairs in the cell, but alter the expression.

The term "global remodeling of the epigenome" refers to where chemical modifications of the genome have occurred where there is no memory of prior gene expression from the differentiated cell from which the reprogrammed cell or iPSC was derived.

The term "incomplete remodeling of the epigenome" refers to where chemical modifications of the genome have occurred where there is memory of prior gene expression from the differentiated cell from which the stable reprogrammed cell or piPSC was derived.

The term "epigenetic reprogramming" as used herein refers to the alteration of the pattern of gene expression in a cell via chemical modifications that do not change the genomic sequence or a gene's sequence of base pairs in the cell.

The term "epigenetic" as used herein refers to "upon the genome". Chemical modifications of DNA that do not alter the gene's sequence, but impact gene expression and may also be inherited. Epigenetic, also called posttranslational modifications or "PTM" to DNA are important, for example, in imprinting and cellular reprogramming. These modifications include, for example, DNA methylation, ubiquitination, phosphorylation, glycosylation, sumoylation, acetylation, S-nitrosylation or nitrosylation, citrullination or deimination, neddylation, OClcNAc, ADP-ribosylation, hydroxylation, fattenylation, ufmylation, prenylation, myristoylation, S-palmitoylation, tyrosine sulfation, formylation, and carboxylation.

The term "pluripotent" as used herein refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell.

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of muiltipotent cells include adult stem cells, such as for example, hematopoietic stem cells and neural stem cells. Multipotent means a stem cell may form many types of cells in a given lineage, but not cells of other lineages. For example, a multipotent blood stem cell can form the many different types of blood cells (red, white, platelets, etc. . . . ), but it cannot form neurons.

The term "multipotency" refers to a cell with the degree of developmental versatility that is less than totipotent and pluripotent.

The term "totipotency" refers to a cell with the degree of differentiation describing a capacity to make all of the cells in the adult body as well as the extra-embryonic tissues including the placenta. The fertilized egg (zygote) is totipotent as are the early cleaved cells (blastomeres).

The term "differentiated cell" is meant any primary cell that is not, in its native form, pluripotent as that term is defined herein. The term a "differentiated cell" also encompasses cells that are partially differentiated, such as multipotent cells, or cells that are stable non-pluripotent partially reprogrammed cells. It should be noted that placing many primary cells in culture can lead to some loss of fully differentiated characteristics. Thus, simply culturing such cells are included in the term differentiated cells and does not render these cells non-differentiated cells (e.g. undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell can be performed both in vivo and in vitro (where in vivo is practiced when an differentiated cell is present within a subject, and where in vitro is practiced using isolated differentiated cell maintained in culture). In some embodiments, where a differentiated cell or population of differentiated cells are cultured in vitro, the differentiated cell can be cultured in an organotypic slice culture, such as described in, e.g., Meneghel-Rozzo et al., (2004), Cell Tissue Res, 316(3); 295-303, which is incorporated herein in its entirety by reference.

As used herein, the term "adult cell" refers to a cell found throughout the body after embryonic development.

In the context of cell ontogeny, the term "differentiate", or "differentiating" is a relative term meaning a "differentiated cell" is a cell that has progressed further down the developmental pathway than its precursor cell. Thus in some embodiments, a reprogrammed cell as this term is defined herein, can differentiate to lineage-restricted precursor cells (such as a mesodermal stem cell), which in turn can differentiate into other types of precursor cells further down the pathway (such as an tissue specific precursor, for example, a cardiomyocyte precursor), and then to an end-stage differentiated cell, which plays a characteristic role in a certain tissue type, and may or may not retain the capacity to proliferate further.

The term "embryonic stem cell" is used to refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "phenotype" refers to one or a number of total biological characteristics that define the cell or organism under a particular set of environmental conditions and factors, regardless of the actual genotype.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not the indicated cells or their progeny as defined by the terms herein.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, and refers to a process of a cell making more copies of itself (e.g. duplication) of the cell. In some embodiments, reprogrammed cells are capable of renewal of themselves by dividing into the same undifferentiated cells (e.g. pluripotent or non-specialized cell type) over long periods, and/or many months to years. In some instances, proliferation refers to the expansion of reprogrammed cells by the repeated division of single cells into two identical daughter cells.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "lineages" as used herein describes a cell with a common ancestry or cells with a common developmental fate. By way of an example only, a cell that is of endoderm origin or is "endodermal linage" this means the cell was derived from an endodermal cell and can differentiate along the endodermal lineage restricted pathways, such as one or more developmental lineage pathways which give rise to definitive endoderm cells, which in turn can differentiate into liver cells, thymus, pancreas, lung and intestine.

A stem cell (e.g., an isolated stem cell such as an embryonic stem cell isolated from a subject) can be contacted with a RAR agonist for any amount of time. For example, a stem cell can be contacted with a RAR agonist for 12 hours, 1 day, 2 days, 3 days, 4 days, 5 days, 6 days, 1 week or more. In one non-limiting example, RAR agonists (dissolved in ethanol or DMSO) are added to MSC cultures at the final concentration between 10 nM and 3 µM, and the volume of RAR agonist solution added to the culture is 0.1%.

Without wishing to be bound by a theory, the contacting a stem cell with a RAR agonist induces or stimulates lineage-directed differentiation of the stem cell into particular lineage. For example, the contacting a stem cell with a RAR agonist can induce or stimulate differentiation into a lineage selected from the group consisting of mesoderm, endoderm, ectoderm, neuronal, mesenchymal, and hematopoietic lineage.

In some embodiments of this and other aspects of the invention, the induced/stimulated lineage is a mesenchymal lineage.

In some embodiments, the induced mesenchymal lineage is selected from the group consisting of myogenic, osteogenic, chodrogenic, tendonogenic, ligamentogenic, maroow stromagenic, adipogenic, and dermogenic.

As used herein, a "mesenchymal stem cell" is a mesenchymal cell having the ability to autoreproduce and to differentiate into one or more mesenchymal cells. Like a mesodermal cell, a mesenchymal stem cell is pluripotent, capable of differentiating into osteoblasts, cartilage cells, myoblasts, fat cells, stroma cells, tendon cells, and the like. While autoreproducing and pluripotent mesodermal cells lose these abilities in the process of development, mesenchymal stem cells are known to persist for a long time in the adult body after it has passed through development.

As used herein, "mesenchymal cells" are ostoblasts, cartilage cells, myoblasts, fat cells, stroma cells, tendon cells and other cells that form mesenchymal tissue, and mesenchymal stem cells which may differentiate into these. Mesenchymal cells occurring during embryogenesis, mesenchymal cells in individual animals, and mesenchymal cells generated by differentiation from pluripotent stem cells in vitro or in vivo are all included in the term "mesenchymal cells."

The stem cells can come or obtained from any source available to the practitioner.

Mesenchymal stem cells can be obtained by a number of methods well known in the art. See for example, U.S. Pat. No. 5,486,358; U.S. Pat. No. 6,387,367; and No. 7,592,174, and U.S. Pat App. Pub. No. 2003/0211602, content of all of which is herein incorporated by reference. Mesenchymal cells can include autologous mesenchymal stem cells, i.e., a cell or cells taken from a subject who is in need of treatment (i.e., the donor and recipient are the same individual). Autologus mesenchymal stem cells have the advantage of avoiding any immunologically-based rejection of the cells. Alternatively, the cells can be heterologous, e.g., taken from a donor. The second subject can be of the same or different species. Typically, when the cells come from a donor, they will be from a donor who is sufficiently immunologically compatible with the recipient, i.e., will not be subject to transplant rejection, to lessen or remove the need for immunosuppression. In some embodiments, the cells are taken from a xenogeneic source, i.e., a non-human mammal that has been genetically engineered to be sufficiently immunologically compatible with the recipient, or the recipient's species. Methods for determining immunological compatibility are known in the art, and include tissue typing to assess donor-recipient compatibility for HLA and ABO determinants. See, e.g., *Transplantation Immunology*, Bach and Auchincloss, Eds. (Wiley, John & Sons, Incorporated 1994).

In some embodiments, the mesenchymal stem cell is derived from a de-differentiated somatic cell (a reprogrammed cell). For example, a somatic cell de-differentiated to a pluripotent stem cell, for example by direct reprogramming of a cell of endodermal origin. Without wishing to be bound by theory, a de-differentiated cell has a morphology that resembles a more primitive cell type from which it was derived, e.g., mesenchymal morphology.

In some embodiments, the mesenchymal stem cell is a re-differentiated mesenchymal stem cell. As used herein, the term "re-differentiated mesenchymal stem cell" refers to a mesenchymal stem cell that is differentiated from a de-differentiated mesenchymal stem cell.

In some embodiments, the mesenchymal stem cells are in a stabilized state, e.g., the cells were taken from a subject and treated in such a manner as to allow them to be stored for some period of time. For example, the cells can be frozen, e.g., using methods known in the art for freezing primary cells, such that the cells are viable when thawed. For example, methods known in the art to freeze and thaw embryos to generate live mammals can be adapted for use in the present methods. Such methods may include the use of liquid nitrogen, e.g., with one or more cryoprotectants, e.g., agents that prevent freeze-thaw damage to the cell.

The population of mesenchymal stem cells obtained from a subject or donor can be substantially pure. The purity of the population can be determined, and manipulated, using methods known in the art. For example, methods using fluorescence activated cell sorting can be used.

Without wishing to be bound by a theory, any suitable cell culture media can be used for in vitro or ex vivo methods of the invention. For example, MSCs can be maintained in α-MEM medium containing 10% fetal bovie serum.

In some embodiments of this and other aspects of the invention, mesenchymal stem cell is a bone marrow-derived mesenchymal stem cell (BMSC).

In some embodiments of this and other aspects of the invention, mesenchymal stem cell is murine marrow derived mesenchymal stem cell.

In some embodiments of this and other aspects of the invention, mesenchymal stem cell is a human mesenchymal stem cell (hMSC).

The inventors have also discovered that RAR agonist treated stem cells can be used for repairing or regenerating muscle. Accordingly, in another aspect, the invention provides a method for muscle repair or regeneration in a subject, the method comprising administering a population of stem cells to a subject, wherein at least one cell in the population has been contacted with a RAR agonist.

In some embodiments, the method comprises steps of: (i) contacting at least one stem cell with a RAR agonist; and (ii) administering said stem cells to a subject, which subject has a damaged muscle tissue.

After contacting the at least 1 stem cell with the RAR agonist for the needed time, treated stem cell can be administered right away or stored for a period of time before administration to a subject. Without limitation, the period of time can range from minutes to days.

The number of RAR agonist treated stem cells to be administered to a subject can range from a single cell to over $10^6$.

Another aspect of the invention relates to a method for muscle repair or regeneration in a subject, the method comprising administering a population of stem cells to a subject, wherein a portion of the stem cells are pre-treated with a RARγ agonist, as described herein. In one embodiment, the portion of pre-treated stem cells is about 50% (a 1:1 ratio). The use of populations of pre-treated stem cells with higher ratios (e.g., 2:1, 3:1, 4:1, 5:1, pre-treated stem cell:untreated stem cell) and also with lower ratios (1:2, 1:3, 1:4, 1:5, pre-treated stem cell:untreated stem cell) is also seen as useful in the method. For example, the portion of pre-treated stem cells can be about 5%, 10%, 15%, 20%, 25%, 30%, 35%, 40%, or 45%. The portion of pre-treated stem cells can also be about 55%, 60%, 65%, 70%, 75%, 80%, 85%, 90% or 95%.

The method of muscle repair or regeneration comprises administering the composition comprising the pre-treated and non-treated stem cells, to a subject at a site of muscle injury, to thereby repair or regenerate the muscle at the site. In one embodiment, the injury is a compound tissue injury. A compound tissue injury is a site of multiple tissue damage, and can include one or more of muscle, bone, tendon, ligament, and fat tissue injury. Various combinations are envisioned. In one embodiment, the compound tissue injury includes muscle and bone. In one embodiment, the compound tissue injury include muscle and at least one additional tissue (e.g., ligaments, tendons, cartilage, bone, skin, fat and blood vessels). In one embodiment, the compound tissue injury include muscle and at least two additional tissues (e.g., two or more of ligaments, tendons, cartilage, bone, skin, fat and blood vessels). In one embodiment, the additional tissue injury includes bone. In one embodiment, the compound tissue injury include muscle and at least three additional tissues (e.g., three or more of ligaments, tendons, cartilage, bone, skin, fat and blood vessels). In one embodiment, the additional tissue injury includes bone. In one embodiment, the compound tissue injury include muscle and at least four additional tissues. In one embodiment, the additional tissue injury includes bone. Additional tissue types other than those described herein may also be included in the injury, in combination with the muscle injury.

As discussed above, the inventors have discovered that progenitor stem cells can be induced to undergo muscle differentiation by acute or chronic exposure to retinoic acid receptor gamma (RARγ) agonists. Accordingly, in one aspect, the invention provides a method of inducing or stimulating lineage-directed differentiation of a stem cell into a single particular lineage, the method comprising contacting a stem cell with a retinoic acid receptor agonist.

In some embodiments, of this and other aspects of the invention, the particular lineage is selected from the group consisting of mesoderm, endoderm, ectoderm, neuronal, hematopoietic lineages, and any combinations thereof.

In some embodiments of this and other aspects of the invention, the particular lineage is a mesenchymal lineage.

In some embodiments of this and other aspects of the invention, the mesenchymal lineage is selected from the group consisting of myogenic, osteogenic, chodrogenic, tendonogenic, ligamentogenic, maroow stromagenic, adipogenic, and dermogenic.

Kits

In another aspect, the invention provides a kit for muscle repair or regeneration. In some embodiments, the kit comprises a RAR agonist. In some embodiments, the kit further comprises a population of stem cells. The RAR agonist can be pre-formulated into a pharmaceutical formulation for administration or ingredients for formulating into a pharmaceutical formulation can be provided in the kit.

In some embodiments, the kit comprises a RAR agonist, wherein the agonist is formulated for topical application.

In some embodiments, the kit comprises a population of stem cells, wherein at least one cell in the population has been pretreated by contacting the cells with a RAR agonist.

In addition to the above mentioned components, the kit can include informational material. The informational material can be descriptive, instructional, marketing or other material that relates to the methods described herein and/or the use of the compound for the methods described herein. For example, the informational material describes methods for administering the formulation to a subject. The kit can also include a delivery device.

In one embodiment, the informational material can include instructions to administer the formulation in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments the individual components of the formulation can be provided in one container. Alternatively, it can be desirable to provide the components of the formulation separately in two or more containers, e.g., one container for an oligonucleotide preparation, and at least another for a carrier compound. The different components can be combined, e.g., according to instructions provided with the kit. The components can be combined according to a method described herein, e.g., to prepare and administer a pharmaceutical composition.

In addition to the formulation, the composition of the kit can include other ingredients, such as a solvent or buffer, a stabilizer or a preservative, and/or a second agent for treating a condition or disorder described herein. Alternatively, the other ingredients can be included in the kit, but in different compositions or containers than the formulation. In such embodiments, the kit can include instructions for admixing the formulation and the other ingredients, or for using the oligonucleotide together with the other ingredients.

The RAR agonists can be provided in any form, e.g., liquid, dried or lyophilized form. It is preferred that the formulation be substantially pure and/or sterile. When the formulation is provided in a liquid solution, the liquid solution preferably is an aqueous solution, with a sterile aqueous solution being preferred. When the formulation is provided as a dried form, reconstitution generally is by the addition of a suitable solvent. The solvent, e.g., sterile water or buffer, can optionally be provided in the kit.

In some embodiments, the kit contains separate containers, dividers or compartments for the formulation and informational material. For example, the formulation can be contained in a bottle, vial, or syringe, and the informational material can be contained in a plastic sleeve or packet. In other embodiments, the separate elements of the kit are contained within a single, undivided container. For example, the formulation is contained in a bottle, vial or syringe that has attached thereto the informational material in the form of a label.

In some embodiments, the kit includes a plurality, e.g., a pack, of individual containers, each containing one or more unit dosage forms of the formulation. For example, the kit includes a plurality of syringes, ampules, foil packets, or blister packs, each containing a single unit dose of the formulation. The containers of the kits can be air tight and/or waterproof.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "elevated," means an increase by a statically significant amount; for the avoidance of any doubt, the term "elevated" means an increase of at least 5%, at least 10%, at least 15%, at least 20%, at least 25%, at least 30%, at least 40%, at least 50%, at least 60%, at least 70%, at least 80%, at least 90%, at least 95%, at least 1-fold, at least 1.5-fold, at least 2-fold, at least 3-fold, at least 4-fold, at least 5-fold, or at least 10-fold or greater as compared to a reference level.

The term "statistically significant" or "significantly" refers to statistical significance and generally means a two standard deviation (2SD) above or below a reference level. The term refers to statistical evidence that there is a difference. It is defined as the probability of making a decision to reject the null hypothesis when the null hypothesis is actually true. The decision is often made using the p-value.

As used herein, the term "ex vivo" refers to cells which are removed from a living organism and cultured outside the organism (e.g., in a test tube).

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective components thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

To the extent not already indicated, it will be understood by those of ordinary skill in the art that any one of the various embodiments herein described and illustrated may be further modified to incorporate features shown in any of the other embodiments disclosed herein.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A method of muscle repair or regeneration in a subject, comprising administering a therapeutically effective amount of a retinoic acid receptor gamma (RARγ) agonist to a subject with damaged muscle tissue, to thereby repair or regenerate the damaged muscle tissue.
2. The method of paragraph 1, wherein said administration is local or systemic.
3. The method of any one of paragraphs 1-2, wherein administration is begun during a time period of increased endogenous retinoid signaling in the subject resulting from incurrence of the damaged muscle tissue.
4. The method of any one of paragraphs 1-3, wherein administration is begun later than 3 days after incurrence of the damaged muscle tissue by the subject.
5. The method of paragraph 4, wherein administration is begun at about 4 days after incurrence of the damaged muscle tissue by the subject.
6. The method of paragraph 4, wherein administration is begun at about 5 days after incurrence of the damaged muscle tissue by the subject.
7. The method of paragraph 4, wherein administration is begun at about 6 days after incurrence of the damaged muscle tissue by the subject.
8. The method of paragraph 4, wherein administration is begun at about 7 days after incurrence of the damaged muscle tissue by the subject.
9. The method of paragraph 4, wherein administration is begun at about 5 days, and is continued through to at least day 7 after incurrence of the damaged muscle tissue by the subject.
10. The method of paragraph 9, wherein administration is continued through to at least day 9 after incurrence of the damaged muscle tissue by the subject.

11. The method of any one of paragraphs 1-10, wherein the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthale nyl) benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy) phenyl]naphthalene-2-carboxylic acid; 5-[(E)-3-oxo-3-(5, 5,8,8-tetrahydronaphthalene-2-yl)propenyl]thiophene-2-carboxylic acid; and enantiomers, derivatives, prodrugs, and pharmaceutically acceptable salts thereof 12. The method of any one of paragraphs 1-11, wherein the damaged muscle tissue is the result of a physical injury or accident, disease, infection, over-use, loss of blood circulation, or muscle atrophy or wasting.

13. The method of any one of paragraphs 1-11, wherein the damaged muscle tissue is dystrophic muscle or an ageing muscle.

14. The method of any one of paragraphs 1-11, wherein the damaged muscle tissue is the result of muscle atrophy/wasting.

15. The method of any one of paragraphs 1-14, wherein the subject is a mammal.

16. The method of any one of paragraphs 1-15, wherein the subject is a mouse.

17. The method of any one of paragraphs 1-15, wherein the subject is human.

18. The method of any one of paragraphs 1-17, further comprising administering an anti-inflammatory agent to the subject.

19. A method of muscle repair or regeneration in a subject, comprising administering pluripotent or multipotent stem cells that have been pre-treated with a RARγ agonist, to a subject at a site of muscle injury, to thereby repair or regenerate muscle at the site.

20. The method of paragraph 19, wherein the muscle injury is a compound tissue injury.

21. The method of paragraph 20, wherein the compound tissue injury comprises an injury to muscle and bone.

22. The method of any one of paragraphs 19-21, wherein the pre-treated stem cells are administered in combination with non-treated stem cells.

23. The method of paragraph 22, wherein the pre-treated stem cells and non-treated stem cells are administered at a ratio of 1:1.

24. The method of any one of paragraphs 19-23, wherein the pre-treated stem cells have been pre-treated with the RARγ agonist for a period of about 3 days.

25. The method of paragraph 19, wherein the pluripotent stem cells are induced pluripotent stem cells.

26. The method of any one of paragraphs 19-25, wherein the pluripotent stem cells are mesenchymal stem cells.

27. The method of any one of paragraphs 19-26, wherein administering is local.

28. The method of any one of paragraphs 19-27, wherein administering is by transplantation of the cells into the subject.

29. The method of any one of paragraphs 19-28, wherein the pluripotent stem cells are autologous or heterologous to the subject.

30. The method of any one of paragraphs 19-29, wherein the pluripotent stem cells are mammalian.

31. The method of any one of paragraphs 19-30, wherein the pluripotent stem cells are rodent.

32. The method of any one of paragraphs 19-30, wherein the pluripotent stem cells are human.

33. The method of any one of paragraphs 19-32, further comprising administering an anti-inflammatory agent to the subject.

34. The method of any one of paragraphs 19-33, wherein the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthale nyl) benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy) phenyl]naphthalene-2-carboxylic acid; 5-[(E)-3-oxo-3-(5, 5,8,8-tetrahydronaphthalene-2-yl)propenyl]thiophene-2-carboxylic acid; and enantiomers, derivatives, prodrugs, and pharmaceutically acceptable salts thereof.

35. The method of any one of claims 19-34 wherein the injured muscle results from physical injury or accident, disease, infection, over-use, loss of blood circulation, or muscle atrophy or wasting.

36. The method of any one of paragraphs 19-34, wherein the injured muscle tissue is dystrophic muscle or an ageing muscle.

37. The method of any one of paragraphs 19-34, wherein the injured muscle is the result of muscle atrophy/wasting.

38. A method of inducing or stimulating myogenic differentiation of isolated mesencymal stem cells in vitro comprising, contacting the mesencymal stem cells with an effective amount of a retinoic acid receptor gamma (RARγ) agonist.

39. The method of paragraph 38, wherein contacting is for a time period selected from the group consisting of about 12 hours, about 1 day, about 2 days, and about 3 days.

40. A method of inducing or stimulating lineage-directed differentiation of a pluripotent stem cell into a mesenchymal lineage, the method comprising contacting the pluripotent stem cell with an effective amount of a retinoic acid receptor gamma (RARγ) agonist.

41. The method paragraph 40, wherein the pluripotent stem cell is an induced pluripotent stem cell.

42. The method any one of paragraphs 40-41, wherein the pluripotent stem cell is a mesenchymal stem cell.

43. The method of any one of paragraphs 40-42, wherein the mesenchymal lineage is selected from the group consisting of myogenic, osteogenic, chodrogenic, tendonogenic, ligamentogenic, maroow stromagenic, adipogenic, and dermogenic.

44. The method of any one of paragraphs 40-43, wherein the pluripotent stem cell is mammalian.

45. The method of any one of paragraphs 40-44, wherein the pluripotent stem cell is rodent.

46. The method of any one of paragraphs 40-45, wherein the pluripotent stem cell is human.
47. The method of any one of paragraphs 40-46, wherein the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthalenyl) benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy) phenyl]naphthalene-2-carboxylic acid; 5-[(E)-3-oxo-3-(5, 5,8,8-tetrahydronaphthalene-2-yl)propenyl]thiophene-2-carboxylic acid; and enantiomers, derivatives, prodrugs, and pharmaceutically acceptable salts thereof.
48. A composition comprising a mesenchymal stem cells wherein a portion of the mesenchymal stem cells have been pretreated by contact with a RARγ agonist to thereby generate pretreated mesenchymal stem cells.
49. The composition of paragraph 43, wherein the portion of pretreated mesenchymal stem cells is selected from the group consisting of 10%, 20%, 30%, 40%, 50%, 60%, 70%, 80%, and 90%.
50. A composition comprising a pluripotent stem cell population, wherein at least one cell of the population was contacted with a RARγ agonist to thereby generate a pretreated pluripotent stem cell.
51. The composition of paragraph 50, wherein the pluripotent stem cell is an induced pluripotent cell.
52. The composition of any one of paragraphs 50-51, wherein the pluripotent stem cell is a mesenchymal stem cell.
53. The composition of any one of paragraphs 50-52, wherein the stem cell is an isolated stem cell.
54. The composition of any one of paragraphs 50-53, wherein the stem cell is mammalian.
55. The composition of any one of paragraphs 50-54, wherein the stem cell is murine.
56. The composition of any one of paragraphs 50-54, wherein the stem cell is human.
57. The composition of any one of paragraphs 50-56, wherein the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthalenyl) benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy) phenyl]naphthalene-2-carboxylic acid; 5-[(E)-3-oxo-3-(5,5,8,8-tetrahydronaphthalene-2-yl)propenyl]thiophene-2-carboxylic acid; and enantiomers, derivatives, prodrugs, and pharmaceutically acceptable salts thereof.
58. A pharmaceutical composition comprising a composition of any one of paragraphs 50-57 and a pharmaceutically acceptable carrier.
59. A kit for repairing or regenerating muscle, comprising at least one of
   (i) a RARγ agonist;
   (ii) a RARγ agonist and a stem cell; or
   (iii) a composition of any one of paragraphs 48-58.
60. The kit of paragraph 59, wherein the stem cell is an induced pluripotent stem cell.
61. The kit of any one of paragraphs 59-60, wherein the stem cell is a mesenchymal stem cell.
62. The kit of any one of paragraphs 59-61, wherein the RARγ agonist is formulated in a pharmaceutical composition.
63. The kit of any one of paragraphs 59-62, wherein the RARγ agonist is formulated for topical application.
64. The kit of any one of paragraphs 59-63, wherein the stem cell is an isolated stem cell.
65. The kit of any one of paragraphs 59-64, wherein the stem cell is mammalian.
66. The kit of any one of paragraphs 59-65, wherein the stem cell is rodent.
67. The kit of any one of paragraphs 59-65, wherein the stem cell is human.
68. The kit of any one of paragraphs 59-67, wherein the RARγ agonist is selected from the group consisting of CD-271 (6-(4-Methoxy-3-tricyclo[3.3.1.13,7]dec-1-ylphenyl)-2-naphthalenecarboxylic acid); CD-394, CD-437 (6-(4-Hydroxy-3-tricyclo[3.3.1.13,7]dec-1-ylphenyl)-2-naphthalenecarboxylic acid); CD-1530 (4-(6-Hydroxy-7-tricyclo[3.3.1.13,7]dec-1-yl-2-naphthalenyl)benzoic acid); CD-2247; palovarotene (4-[(E)-2-[5,6,7,8-Tetrahydro-5,5,8,8-tetramethyl-3-(1H-pyrazol-1-ylmethyl)-2-naphthalenyl]-ethenyl]-benzoic acid); BMS-270394 (3-Fluoro-4-[(R)-2-hydroxy-2-(5,5,8,8-tetramethyl-5,6,7,8-tetrahydro-naphthalen-2-yl)-acetylamino]-benzoic acid); BMS-189961 (3-Fluoro-4-[2-hydroxy-2-(5,5,8,8-tetramethyl-5,6,7,8-tetrahydro-naphthalen-2-yl)-acetylamino]-benzoic acid); CH-55 (4-[(E)-3-(3,5-Di-tert-butyl-phenyl)-3-oxo-propenyl]-benzoic acid); 6-[3-(adamantan-1-yl)-4-(prop-2-ynyloxy)phenyl]naphthalene-2-carboxylic acid; 5-[(E)-3-oxo-3-(5,5,8,8-tetrahydronaphthalene-2-yl) propenyl]thiophene-2-carboxylic acid; and enantiomers, derivatives, prodrugs, and pharmaceutically acceptable salts thereof.
69. The kit of any one of paragraphs 59-68, further comprising instructions for use.

The present invention is further illustrated by the following Examples. These Examples are provided to aid in the understanding of the invention and are not construed as a limitation thereof.

EXAMPLES

Example 1

Methods

Isolation and Culture of Bone Marrow Derived Mesenchymal Stem Cells (MSCs).

MSCs were isolated as described previously (ref) with minor modification. Briefly, mouse bone marrow cells (1–2× $10^7$) harvested from long bones of 4-6 weeks old mice were seeded onto 100-mm culture dishes, incubated for 3 hours at 37° C. to allow attachment of adherent cells, and then rinsed twice with PBS to remove the nonadherent cells. The bone marrow-derived MSCs formed adherent colonies after 12-15 days of culture. Primary cultures were passed to disperse the colony-forming cells (passage 1). The cells were then subcultured again when they reached 70% confluent. Cells were maintained in α-MEM (Gibco BRL; Invitrogen Corp.) containing 20% fetal bovine serum (FBS; Equitech-Bio Inc.), 2 mM L-glutamine, a combination of 100 U/ml penicillin and 100 µg/ml streptomycin (Biofluids Inc.), and 55 µM 2-mercaptoethanol (Gibco BRL; Invitrogen Corp.) before the first passage. After the first passage, cells were maintained in 10% FBS, α-MEM unless indicated.

DsRED expressing MSCs were isolated from B6.Cg-Tg (CAG-DsRed*MST)1Nagy/J mice (Jax Mice). GFP expressing MSCs were obtained from the transgenic mice carrying H2K-GFP (Dominici et al. Genesis 42:17-22(2005)).

Cell Transplantation. MSCs ($1\times10^5$) with or without RAR agonist pretreatment were suspended in 10 µl serum-free DMEM and placed onto the muscle defect created as described herein.

Histological Procedures. To inspect muscle tissue structure, samples were fixed in 4% PFA and embedded in paraffin. Five µm serial sections were stained by either H&E (http://www.ihcworld.com/_protocols/special_stains/HE_Mayer.htm) or Masson's trichrome staining solution (http://www.ihcworld.com/_protocols/special_stains/masson_trichrome.htm). To detect adipose tissue, 4% PFA fixed samples were equilibrated in 20% sucrose in PBS, embedded in OCT compound and then sectioned by cryostat. Ten µm cryosections were dried, rehydrated and then stained with Oil-red O (http://www.ihcworld.com/_protocols/special_stains/oil_ red o.htm).

Immuno-Fluorescence. For the detection of various antigens in tissue sections, 5 µm paraffin sections were de-paraffinized, re-hydrated and then treated with 0.1% pepsin in 0.02 N HCl for 15 min at 37° C. Sections were washed three times in PBS-T and blocked in 10% normal goat serum with 0.3% BSA. Sections were incubated with 1st antibody, washed three times with PBS-T and then incubated with $2^{nd}$ antibody. The list of antigens, antibodies and their dilutions are shown below.

MyoD: Anti-MyoD; sc-760 (Santa Curz, 1:100), Anti-Rabbit Alexa Flour 488 (Invitrogen, 1:500)

Myf5: Anti-Myf5; sc-302 (Santa Curz, 1:100), Anti-Rabbit Alexa Flour 488 (Invitrogen, 1:500)

Anti-Laminina2; ALX-804-190 (Enzo Life Science, 1:250), Anti-Rat Alexa Flour 594 (Invitrogen, 1:500)

Myosin heavy chain (MHC): Anti-MHC; MF-20 (Developmental Studies Hybridoma Bank, 1:25), Anti-mouse Alexa Flour 588 (Invitrogen, 1:500)

Osteocalcin (OC): Anti-OC; M173 (Takara, 1:500), Anti-Rabbit Alexa Flour 594 (Invitrogen, 1:500)

Green fluorescent protein (GFP): Biotin conjugated Anti-GFP; NB100-1678 (Novus, 1:250), Streptavidin Alexa Flour 488 (Invitrogen, 1:500)

Local and Systemic Administration of RAR Agonist. Systemic administration of RAR agonist was carried out by gavage as described previously (Shimono et al. J. Orthop. Res. 28:271-277, 2010). Local delivery of RAR agonist was done by injecting RAR agonist (dissolved in DMSO) using Hamilton syringe 87943 with 26G needle.

Results

The differential effects of retinoid agonists on myogenic differentiation in mouse bone marrow-derived mesenchymal stem cell (BMSC) cultures were investigated. BMSCs were prepared from femurs and tibias of 6 week-old mice by standard methods and maintained in 5% FBS DMEM for 7 days in presence of 0.1% DMSO (vehicle: Control), 1 µM all-trans retinoic acid (RA) (commercially available from Sigma), 1 µM RAR alpha-agonist (obtained from NuRx Pharmaceuticals) or 30 nM RAR gamma-agonist (CD1530, commercially available). Many elongated multinucleated muscle cells formed only in RAR gamma-agonist treated cultures.

Cells from a mesenchymal stem cell line were cultured for 10 days in the presence or absence of RAR gamma-agonist (CD1530, 100 nM). Cultures were processed for immunostaining with MyoD or Myf5 antibodies or stained with nuclear dye DAPI. Control untreated cells contained undetectable amounts of MyoD and Myf5, but both proteins were clearly present in gamma-agonist treated cultures. Results indicated an increase in MyoD and Myf5 levels by the RAR gamma-agonist in mesenchymal stem cell (MSC) cultures.

A muscle defect mouse model was used to investigate the muscle repair stimulation by administration of RAR gamma-agonists. A round-shaped defect was created with an electric cautery in calf or anterior tibial muscles in 8 week-old mice resulting in a 2.0 mm×2.0 mm×2.0 mm defect.

Round-shaped defects were created in calf-muscle tissue of 8 weeks old mice as above (one muscle defect/mouse). Mice received corn-oil (vehicle) or 300 µg RAR gamma agonist (CD1530)/day by gavage on day 8, 10 and 12 after injury. Tissue was collected for histological analysis on day 14. Muscle defects in control mice were largely filled with scar-like fibrous and connective tissues by day 14. These scar-like tissues were totally negative for myosin heavy chain (MHC) as detected by immunostaining. In contrast, the muscle defect sites in RAR gamma-agonist treated mice were filled with many elongated muscle-like cells and many of these cells were MHC positive. Results indicate stimulation of muscle repair by systemic administration of RAR gamma-agonist.

Following creation of 2×2×2 mm defect in the center of anterior tibial muscle as above (one muscle defect/mouse), mice received corn-oil (vehicle) or 300 µg RAR gamma agonist/day by gavage on day 8, 10 and 12 after injury. Tissues were collected for histological analysis at 2 and 4 weeks. Macro-photos of injured muscle tissue collected from control and RAR gamma-agonist (CD1530)-treated mice were taken at 4 weeks after injury. In controls, the defect was clearly visible as a white spot. In contrast, there was almost no visible sign of the original defect in the RAR gamma-agonist treated mice. Histological analysis revealed that the muscle tissue defects in control mice were occupied by mixtures of adipose and fibrous tissue at 2 and 4 weeks. Deposition of fibrous tissue was also noted between muscle fibers. However, in the RAR gamma-agonist treated mice, the muscle defects were filled with muscle fibers aligned along the major longitudinal axis of the anterior tibial muscle. Results indicated full repair of muscle defects by systemic administration of RAR gamma-agonist over time.

Histological analysis of skeletal muscle tissue was performed 4 weeks after injury. Serial transverse sections of muscle tissue specimens collected 4 weeks after injury (same samples as discussed directly above) were stained with Masson's trichrome or processed for immuno-staining with antibodies to laminin (an extracellular protein abundant around muscle cells). In controls, the initial injury site was poorly repaired and largely occupied by adipose tissue and fibrous connective tissue that did not stain with anti-laminin antibodies. In contrast, the muscle injury was almost completely repaired in gamma-agonist treated animals; the repair tissue stained strongly with anti-laminin antibodies. To evaluate and quantify the changes of skeletal muscle tissue structure, images of trichrome-stained serial sections were taken and the relative amounts of muscle fiber, adipose and fibrous tissues were determined in multiple defined areas by ImagePro software. The analyzed areas were 9×9 grids each (about 3×3 mm) that included the original injured site (2×2 mm). Muscle injury caused a decrease in total muscle fiber area and a concurrent increase in fibrous and adipose tissues area. In contrast, CD1530 treatment largely restored the tissue composition. The relative amount of muscle as determined is shown graphically in FIG. 1.

To verify that the RARgamma is required for muscle repair and regeneration, muscle injuries were created in wildtype (WT) and RARgamma-null mice as above. The animals were then treated with gamma-agonists or vehicle (corn oil). Tissue samples were collected 4 weeks after injury, sectioned and stained with Masson's trichrome staining solution. In agreement with the above discussed results, gamma-agonist treatment induced effective muscle repair in WT mice. However, it had minimal effects in RARgamma-null mice in which the muscle defect site was filled with adipose and some connective tissue cells and lined with fibrous cells. These findings indicate that: (1) the muscle repair effects by the gamma-agonists are mediated by RARgamma; and (2) RARgamma is required for repair of skeletal muscle tissue.

Figure 2:
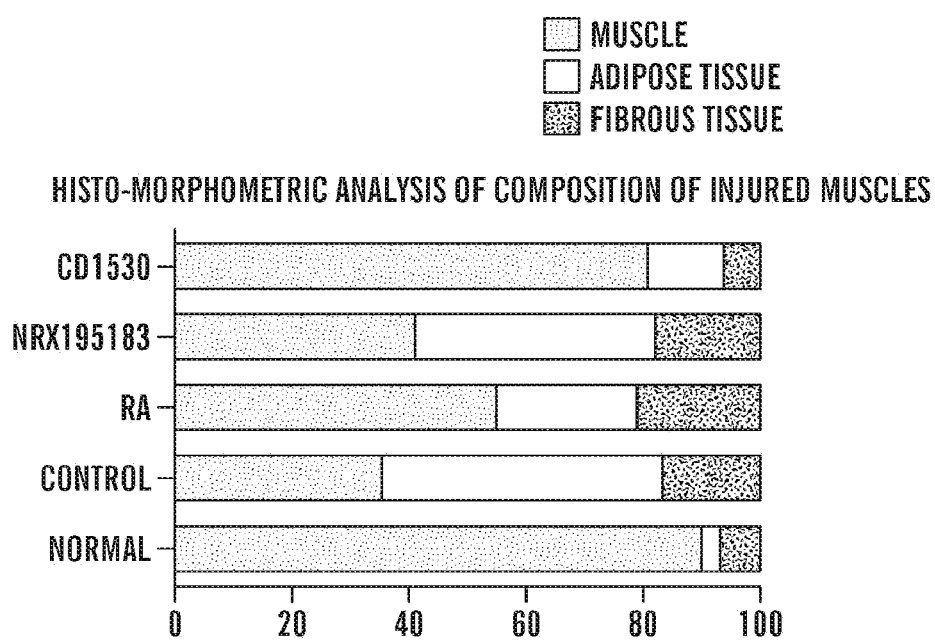
FIG. 2 is a graphical representation of data obtained from histo-morphometric analysis of the composition of injured muscle.

The effects of various retinoid agonists on skeletal muscle repair were examined Macro photographs were taken of muscle injury sites at the 4-week time point. Histo-morphometric analysis of composition of injured muscles is shown in FIG. 2. Muscle injury defects were created in 8 week-old mice as described above. Mice received corn oil (control), 300 μg pan-agonist retinoic acid (RA), 900 μg NRX195183 (RARalpha agonist) or 300 μg CD1530 (RARgamma agonist) on day 8, 10 and 12 by gavage. Four weeks after injury, tissue samples were collected, processed for histological analysis and subjected to histomorphometric quantification. In control animals and RARalpha-agonist- or RA-treated animals, the injury sites were still clearly visible as large whitish spots due to the replacement of muscle with adipose tissue. However, in the RARgamma-treated animals, the injury sites were essentially invisible at 4 weeks since they had been filled with repair muscle tissue. To quantify the responses, serial sections of tissues at the repair site were stained with trichrome and analyzed for quantification of relative amounts of muscle, adipose and fibrous tissues in defined areas by ImagePro software as described above. The analyzed areas were 9×9 grids each (about 3×3 mm) that contained the original injury site (2×2 mm). Results are shown in FIG. 2. The graph shows averages of nine sections from three mice. "Normal" was derived from a muscle tissue composition of uninjured normal muscle. As to be expected, muscles in control animals were composed of 90% muscle tissue, 7% fibrous tissue and trace amount of fat tissue. The muscle injury caused a dramatic decrease in muscle fiber area from 90% to 33%, and there were corresponding increases in adipose and fibrous tissue areas. Treatment with RA moderately improved muscle fiber area from 33% (control) to 54%, but there was a significant increase of fibrous tissue area. The RAR alpha agonist NRX195183 did not improve tissue composition. In contrast, the composition of repair tissues in CD1530-treated animals was almost normal.

The effects of RARgamma agonists with different backbone structure on muscle repair was investigated. In the experiments discussed above, the gamma-agonist CD1530 was shown to dramatically accelerate muscle repair and that RARgamma expression is required for such effect. To further validate these findings and identify possible more potent gamma-agonists, three other structurally different selective RARgamma agonists (BMS270394, Palovarotene, and CD437) were tested in muscle repair. Leg muscle injuries were created as above. Each group of mice received one of the different agonists (100 μg/gavage/day) or vehicle at day 8, 10 and 12 from injury. Tissues were collected 4 weeks after surgery and examined as above. In controls, the muscle injury sites were clearly visible as whitish spots and there was minimal muscle repair; in addition, fibrous scar tissue was present within the injured muscle. In contrast, each gamma-agonist induced effective muscle repair; among the three agonists tested, BMS270394 was the most effective and completely restored to normal muscle structure. The results indicate that gamma-agonists are extremely effective in triggering muscle repair.

The effects of local administration of RARgamma agonist on muscle repair were examined. Although major side effects of systemic administration of gamma agonists have not been observed in the muscle repair experiments, it could be necessary to delivered them locally in certain clinical situations. To test the effectiveness of these drugs when given locally, muscle injuries were created as above and 3 μg of CD1530 was injected subcutaneously around the injury site on day 8 and 10 after operation. Vehicle was injected in controls, and tissues were collected at 4 weeks and examined as above. In controls, the injury sites were clearly visible and largely occupied by adipose tissue. In CD1530-treated group, however, the muscle defects were almost completely repaired. The molecular weight of the gamma-agonists is in general less than 500 and therefore, the drugs could be delivered from skin to deeper muscle tissues in the form of ointments or other formulations (in addition to local injection).

GFP-expressing mouse mesenchymal stem cells were treated with vehicle (control) or 100 nM CD1530 for three days in culture, mixed with Matrigel and 1 μg rhBMP2, and then transplanted into nude mice. Two weeks after implantation, ectopic tissue masses were collected for analysis. Massive endochondral bone formation was observed in controls; anti-GFP and anti-OC (osteocalcin) immunostaining revealed that the transplanted MSCs had contributed to bone formation. However, no ectopic endochondral bone had formed in mice transplanted with gamma-agonist-pretreated MSCs; these cells were present as indicated by positive GFP staining but were negative for OC staining and were often aligned. Some cells were fused or in the process of fusion. Thus, the gamma agonist treatment effectively primes MSCs to undertake a myogenic differentiation pathway. These results indicate that RARgamma agonist is a priming factor for myogenic differentiation of mesenchymal stem cells (MSC).

To further examine the ability of gamma agonists to prime MSCs towards the myogenic lineage, muscle injury defects were created in nude mice as discussed above and DsRed-expressing MSCs pretreated with gamma-agonist for three days (or left untreated) were transplanted thereto. Two weeks after transplantation, tissues present at injury sites were collected and inspected under fluorescent stereomicroscope. Tissues were then processed for histological analyses. Fluorescent stereomicroscopy revealed strong red fluorescence signal present in muscle injury sites where gamma-agonist-pretreated MSCs were implanted, but little to no fluorescence was observed in sites implanted with control untreated MSCs (A, left panels). Staining with oil red O revealed the presence of abundant adipose tissue in injury sites implanted with control MSCs (B, left), but absence of these cells in the sites implanted with gamma-agonist-pretreated MSCs (B, right). Immunofluorescence analysis revealed that DsRed-positive and gamma-agonist-pretreated MSCs contributed to the formation of MHC-expressing muscle repair tissue (C, right), but their absence in control. (DsRed, red color; MHC, green;

DAPI, purple) In experiments described above, systemic administration of gamma-agonists induced repair of muscle injury defects in 4 weeks. It is noteworthy that similar defects were almost completely repaired within 2 weeks after transplantation of gamma-agonist primed MSCs. Therefore the use of gamma-agonist pretreated MSCs could represent a very effective procedure to repair muscle injuries quickly. These results indicate repair of muscle injury by gamma-agonist-primed MSCs.

Example 2

Methods

Unless otherwise indicated, all methods were performed as described in Example 1, or by standard procedures known in the art.

Immunodetection of human cells and myosin heavy chain was performed by incubating sections with biotinylated anti-human TRA-1-85 (1:250 dilution, R&D cat #BAM3195) and anti-laminin (1:250, Enzy, ALX-804-190), washed and then incubated with Alexa Fluor 488streptavidine and Alexa Fluor 594 anti-rat IgG.

Results

Repair of Muscle Injury by Gamma-Agonist-Pre-Treated Human Adipose Tissue Derived Mesenchymal Stem Cell.

The experience described below indicate that RAR γ agonist pre-treated stem cells not only regenerate muscle tissue by themselves, but also support myogenic differentiation of host cells. As such, these cells are now referred to as "pre-treated" rather than "primed" mesenchymal stem cells, to be consistent with the accepted definition of the term "prime" as it is used in the art to mean to commit cells to undergo myogenesis.

To test the effects of pretreatment of an human mesenchymal stem cell with RAR gamma-agonist, a round-shaped defect was created in the anterior tibial muscle of NOD mice (NOD.Cg-Rag1tm1Mom Prf1tm1Sdz/Sz) as described above. Non-treated or RARg treated human adipose derived mesenchymal stem cells were transplanted to the site (5,000 cells per site). Tissue was collected 2 weeks after operation and subjected to histological analyses by Masson's trichrome staining sections of RARg pretreated MSC transplanted muscle and control MSC transplanted muscle, and also by immunol-fluorescence detection of myosin heavy chain (MHC, anti-human-derived cell antigen, and nucleus (DAPI) of RARg pretreated MSC transplanted muscle and control MSC transplanted muscle.

RARg pretreated human MSC clearly facilitated repair of the damaged muscle tissue. While RARg pretreated human MSCs contributed muscle tissue regeneration, MSCs that were not pre-treated were mostly excluded from the muscle tissue.

To test if RAR gamma-agonist pre-treatment is effective on different type of mesenchymal stem cells, human adipose tissue derived mesenchymal stem cells (Zenbio, Cat # ASC-F) were treated with 1 μM CD1530 or vehicle for 3 days in vitro, and then transplanted into a muscle damage model system. A round-shaped defect was created in the anterior tibial muscle of 6-week old NSG mice (NOD scid gamma mouse, Jax mice #005557) as described above (NOD.Cg-Prkdc$^{scid}$ Il2rg$^{tm1Wjl}$/SzJ). Non-treated or RARg treated human adipose derived mesenchymal stem cells were transplanted to the site (10,000 cells per site). Tissue was collected 2 weeks after operation and subjected to histological analyses (Masson's trichrome staining sections of RARg primed MSC transplanted muscle and control MSC transplanted muscle, and also by immuno-fluorescence detection of laminin, human-derived cell antigen, and nucleus (DAPI) of RARγ agonist pretreated MSC transplanted muscle and control MSC transplanted muscle.

RARg pre-treated human MSC clearly facilitated repair of the damaged muscle tissue. While RARγ pretreated human MSCs were observed to be mainly distributed around muscle fibers, non-treated cells were mostly excluded from the muscle tissue. These results indicate that the use of RARγ agonist pretreated stem cells such as MSC is an effective therapy for muscle repair and also that stem cells (e.g. MSC) from various sources can be used for this therapy.

Repair of Complex Tissue (Muscle+Bone) Injury with Primed (RARg Agonist Treated) or Non-Primed MSCs Sever muscle injury often accompanies damages of other tissue such as bone, tendon and nerve. By using a simplified compound injury model, RARγ agonist treated MSCs were examined for preferential targeting to injured muscle tissue.

Compound (bone and muscle) tissue injury was created in 2 month old mice by cutting fibula and surrounding muscle tissue. Following this, a 1:1 mixture of RARγ agonist pre-treated MSC and control non-pretreated MSCs were transplanted near the injury site. The MSC were prepared either from GFP (pre-treated) or DsRED (non-treated) expressing mice bone marrow. The injured tissue were collected 1 week after surgery, sectioned and examined for distribution of pre-treated and non-pretreated MSCs using anti-GFP and anti-DsRed antibodies respectively. Histological analysis with HE staining revealed damaged bone and muscle tissues were still under repair process. Strikingly, while the majority of primed MSCs were detected in muscle tissue, the majority of primed cells were always associated with bone tissue. Some of the DsRed expressing RARγ agonist pretreated MSCs were observed to form typical multinucleated skeletal muscle cells.

The RARγ agonist pre-treated and non-treated MSCs were observed to target different tissue injury sites. The results indicate that RARγ agonist pretreated MSCs selectively target injured muscle tissue. RARγ agonist pretreated MSCs will be useful to repair damaged muscle tissue when other tissues are also damaged. It has previous been reported that systemic administration of RARγ agonist not only inhibits heterotopic ossification but delays fracture healing (Shimono et al., Nature Medicine 17, 454-460 (2011)). In addition these results strongly suggest that the combined transplantation of pre-treated and nontreated MSCs at an appropriate ratio is an effective therapy for compound tissue injury.

Requirement of RARγ Signaling in Muscle Repair

The above results indicate that muscle tissue defect is poorly repaired in RARγ null mice. To further confirm this finding, another widely used muscle degeneration model was used. 1 μg cardio-toxin was injected into anterior tibial muscle tissue of wild type and RARγ null mice. Muscle tissue was collected two weeks after cardio-toxin injection, sectioned and examined by Masson's trichrome staining. The cardio-toxin injected muscle tissue was seen to be mostly restored with immature muscle fibers by 2 weeks in the control wild type mice. In contrast, RARγ null muscle tissue was seen to be poorly repaired.

Up-Regulation of Local Retinoid Signaling after Muscle Injury

Anterior tibial muscle of the retinoic acid signaling reporter mice (RARE-LacZ mice) were cut or sham-operated. The muscle tissue was collected at days 1, 4 or 7 and stained with X-gal. The reporter activity was observed to be increased 4 days after injury, suggesting the involvement of this signaling pathway in muscle tissue repair.

Figure 4:
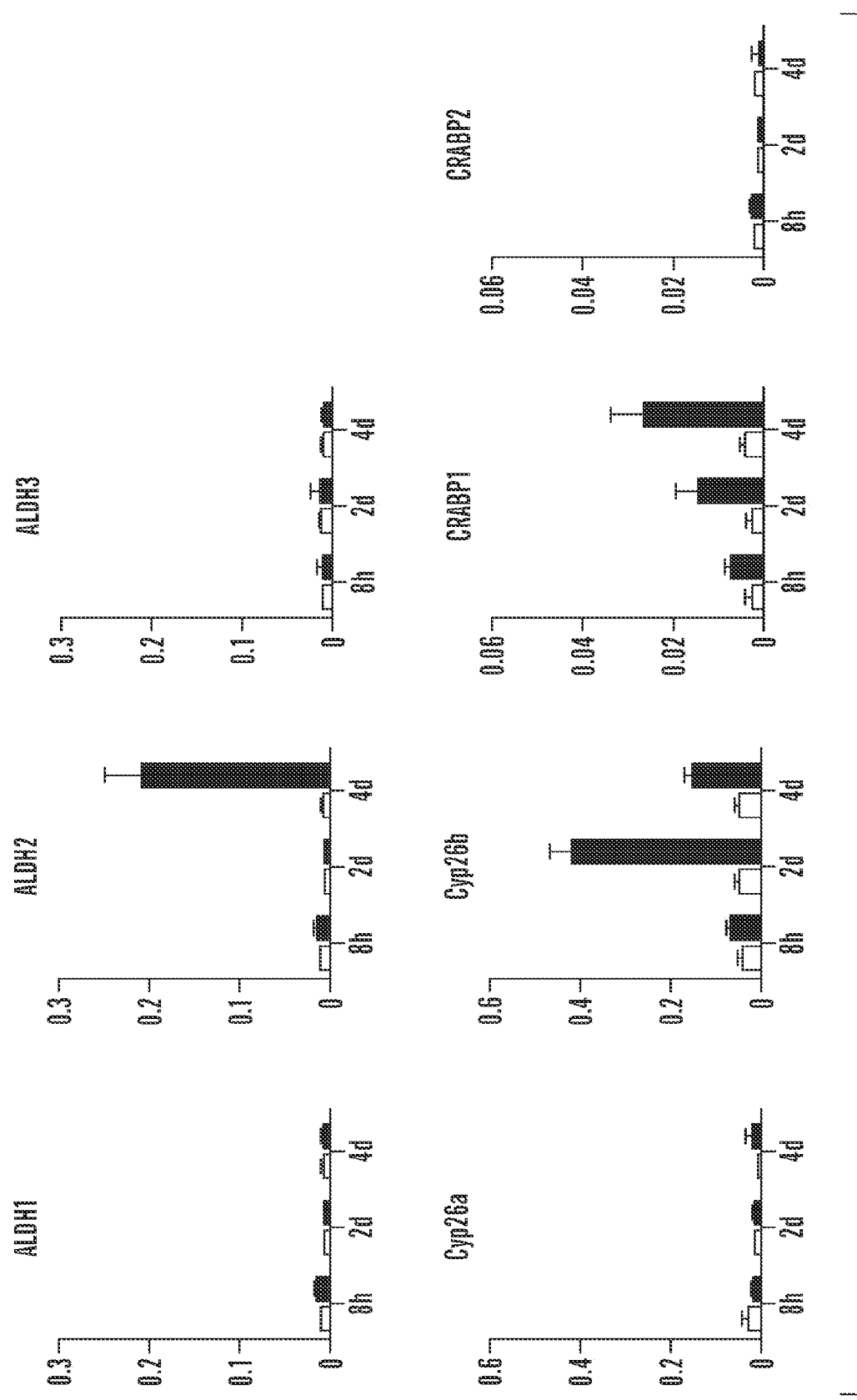
FIG. 4 is a series of bar graphs with data from experimental results that indicate the local RA concentration decreases first and then transiently increases after muscle injury.
Figure 5:
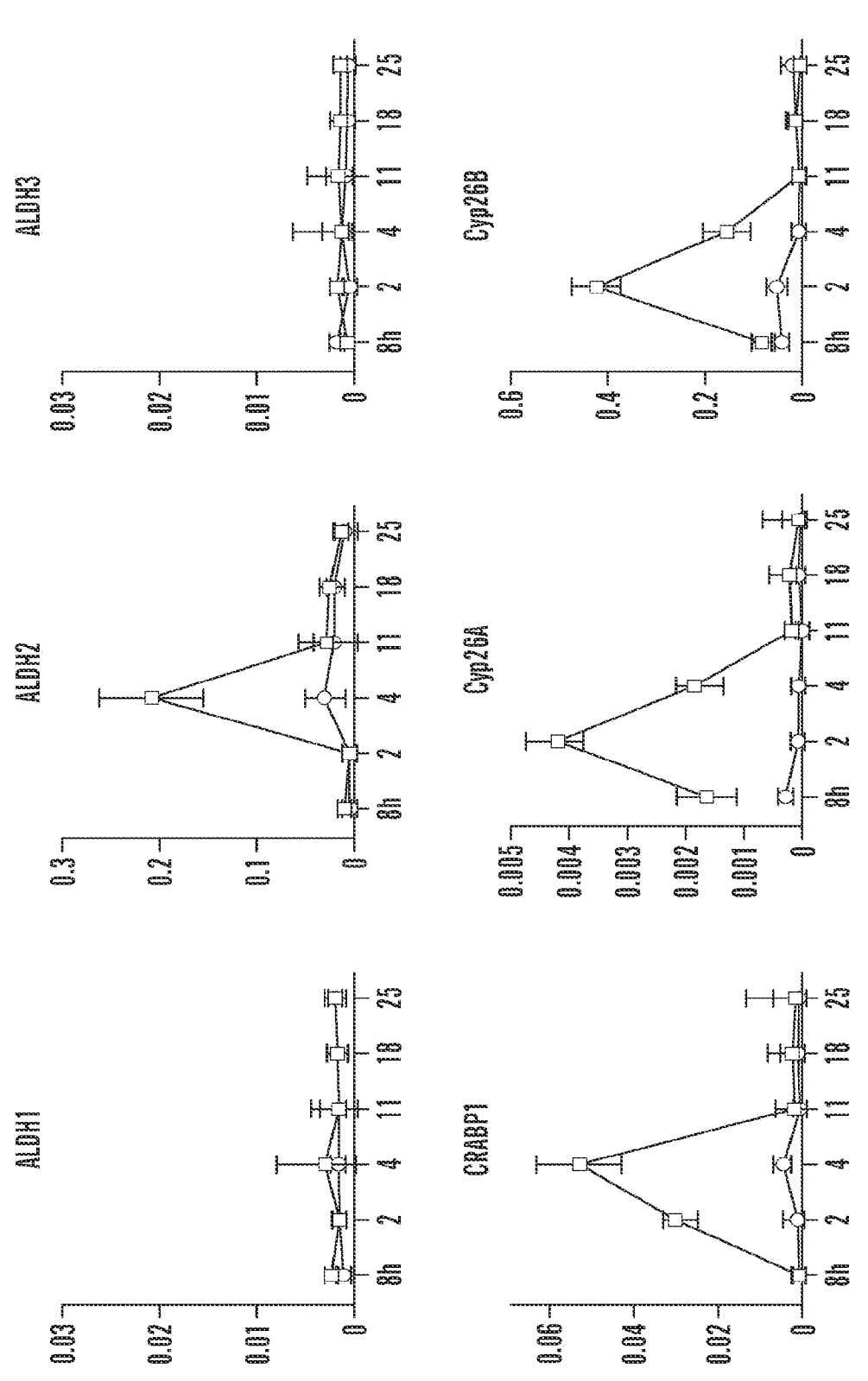
FIG. 5 is a series of line graphs with data from experimental results that indicate the local RA concentration decreases first and then transiently increases after muscle injury.

Total muscle tissue RNA was collected at 8 hours, 2 days and 4 days, and subjected to RT-PCR for the analysis of RAR signaling related gene expression. The expression of ALDH2, the late limiting enzyme that produces RA from its precursor was seen to be up-regulated 4 days after injury, returning back to normal expression levels by day 11. In contrast, Cyp26b1 (Cyp26B), the enzyme that degrades RA was seen to be transiently up-regulated at day 2 after injury. The results are shown in FIGS. 4 and 5, and indicate that the local RA concentration decreases first and then transiently increases after muscle injury.

Effect of the Treatment Timing on Muscle Tissue Repair

Muscle defects were created as described above. Mice were treated with RARg agonist (CD1530) at days 1-3 or days 5-7. Pictures show the HE staining of the muscle tissues of 4 weeks after injury. Muscle defects in untreated controls were largely replaced with fat and fibrous tissue. The Day 1-3 treatment with RARg agonist decreased adipose and fibrous scar tissue formation but left a partial defect. In contrast, the muscle defects were completely filled with newly generated muscle fibers in the Day 5-7 treatment group. Thus the treatment timing is very important for faster and better muscle tissue repair. RARg signaling should be enhanced when endogenous retinoid signal is increased. The suggested treatment regimen is local or systemic administration of RARg agonist on day 5 and 7 after muscle injury. Further enhancement of accurate treatment timing can be achieved by measuring local retinoic acid concentration by LS/MS/MS.

Muscle defects were created as described above. Mice were given 100 ng RARγ agonist (CD1530) every other day during the period of days 1-5, days 5-9, and days 1-9. Day 1-5 group mice received CD1530 on day 1, 3 and 5. Day 5-9 group received CD1530 on day 5, 7 and 9. Day 1-9 group received CD1530 on day 1, 3, 5, 7 and 9. The muscles were then compared to vehicle treated injured muscle as well as intact muscle (un-injured muscle) tissue. The HE staining of the muscle tissues at 4 weeks after injury was examined. Muscle defects in untreated control were observed to be largely replaced with fat and fibrous tissue (Vehicle). Both day 1-5 or 1-9 treatment with RARγ agonist decreased adipose and fibrous scar tissue formation but left a large indentation. The quality and the amount of newly formed muscle tissue were best in the Day 5-9 treatment group, which had a much reduced indentation.

Histo-Morphometric Analysis of the Injured Muscle Tissue

Figure 6:
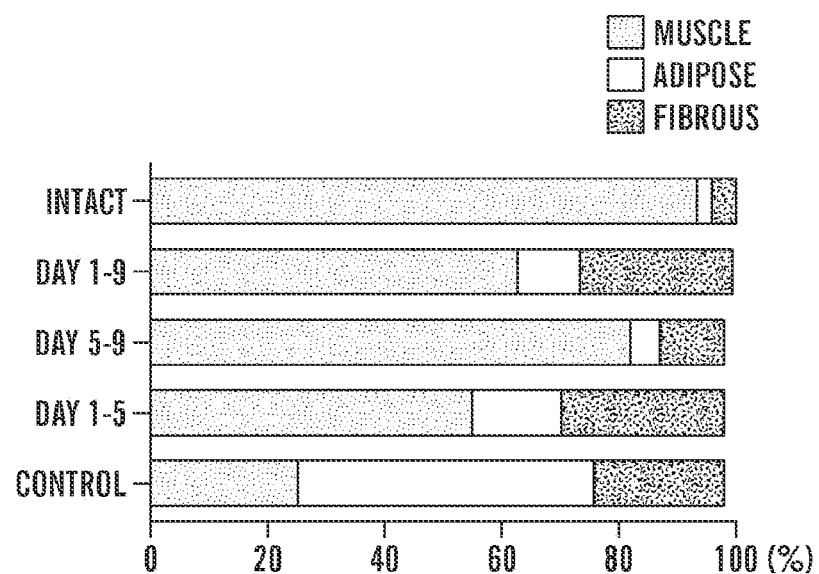
FIG. 6 is a bar graph of data obtained from the histological analysis of skeletal muscle tissue 4-week after injury following the indicated treatment times with RARγ agonist. On the graph, the left filled in segment indicates muscle. The segment to the direct right of that is shown as open (white) and indicates adipose. The segment to the right of that, filled in, indicates fibrous tissue.

Serial tissue sections at the repair site were stained with Masson's trichrome and analyzed to quantify relative amounts of muscle, adipose and fibrous tissues in defined areas by ImagePro software as described. Results are shown in FIG. 6. Image analysis confirmed that Day 5-9 treated group muscle tissue contains the least amount of adipose and fibrous tissue among all injured groups. This indicates that the treatment timing is very important for faster and better muscle tissue repair and that more beneficial results are obtained when RARγ signaling is therapeutically enhanced (e.g., by administration of an RARγ agonist) at the time of increased endogenous retinoid signaling, and not before.

We claim:

1. A method of muscle repair or regeneration in a subject with damaged muscle tissue, comprising administering a therapeutically effective amount of a retinoic acid receptor gamma (RARγ) agonist to a subject with damaged muscle tissue, to thereby repair or regenerate the damaged muscle tissue, wherein the RARγ agonist is 4-[(E)-2-[5,6,7,8-Tetrahydro-5,5,8,8-tetramethyl-3-(1H-pyrazol-1-ylmethyl)-2-naphthalenyl]-ethenyl]-benzoic acid or a pharmaceutically acceptable salt thereof.

2. The method of claim 1, wherein said subject in need thereof has a muscle damaging myopathy.

3. The method of claim 2, wherein the muscle damaging myopathy is an inflammatory myopathy.

4. The method of claim 3, wherein the muscle damaging myopathy is myositis ossificans.

5. The method of claim 2, wherein the muscle damaging myopathy is a muscular dystrophy.

6. The method of claim 1, wherein the subject has damage to skeletal muscle.

7. The method of claim 1, wherein said RARγ agonist is administered locally.

8. The method of claim 1, wherein said RARγ agonist is administered systemically.

9. A method of inducing progenitor stem cells to undergo myogenic differentiation in a subject with damaged muscle tissue, comprising administering a therapeutically effective amount of an RARγ agonist to the subject, wherein the RARγ agonist is 4-[(E)-2-[5,6,7,8-Tetrahydro-5,5,8,8-tetramethyl-3-(1H-pyrazol-1-ylmethyl)-2-naphthalenyl]-ethenyl]-benzoic acid or a pharmaceutically acceptable salt thereof.

10. The method of claim 9, wherein said subject in need thereof has a muscle damaging myopathy.

11. The method of claim 10, wherein the muscle damaging myopathy is an inflammatory myopathy.

12. The method of claim 11, wherein the muscle damaging myopathy is myositis ossificans.

13. The method of claim 10, wherein the muscle damaging myopathy is a muscular dystrophy.

14. The method of claim 9, wherein the subject has damage to skeletal muscle.

15. The method of claim 9, wherein said RARγ agonist is administered locally.

16. The method of claim 9, wherein said RARγ agonist is administered systemically.

17. A method for reducing muscle tissue damage in a subject with a muscle damaging myopathy, said method comprising administering to said subject an RARγ agonist in amount sufficient to reduce said muscle tissue damage wherein the RARγ agonist is 4-[(E)-2-[5,6,7,8-Tetrahydro-5,5,8,8-tetramethyl-3-(1H-pyrazol-1-ylmethyl)-2-naphthalenyl]-ethenyl]-benzoic acid or a pharmaceutically acceptable salt thereof.

18. The method of claim 17, wherein the subject has damage to skeletal muscle.

19. The method of claim 17, wherein the muscle damaging myopathy is an inflammatory myopathy.

20. The method of claim 19, wherein the muscle damaging myopathy is myositis ossificans.

21. The method of claim 17, wherein the muscle damaging myopathy is a muscular dystrophy.

22. The method of claim 17, wherein said RARγ agonist is administered locally.

23. The method of claim 17, wherein said RARγ agonist is administered systemically.

* * * * *